(12) United States Patent
Miller

(10) Patent No.: US 8,690,791 B2
(45) Date of Patent: Apr. 8, 2014

(54) APPARATUS AND METHOD TO ACCESS THE BONE MARROW

(75) Inventor: Larry J. Miller, Spring Branch, TX (US)

(73) Assignee: Vidacare Corporation, Shavano Park, TX (US)

( * ) Notice: Subject to any disclaimer, the term of this patent is extended or adjusted under 35 U.S.C. 154(b) by 654 days.

(21) Appl. No.: 12/427,310

(22) Filed: Apr. 21, 2009

(65) Prior Publication Data

US 2009/0204024 A1 Aug. 13, 2009

Related U.S. Application Data

(63) Continuation of application No. 11/427,501, filed on Jun. 29, 2006, now Pat. No. 7,951,089.

(51) Int. Cl.
*A61B 10/00* (2006.01)

(52) U.S. Cl.
USPC .......................................... 600/562; 600/566

(58) Field of Classification Search
USPC .................................................. 600/562, 566
See application file for complete search history.

(56) References Cited

U.S. PATENT DOCUMENTS

| | | | |
|---|---|---|---|
| 1,539,637 A | 5/1925 | Bronner | 433/81 |
| 2,317,648 A | 4/1943 | Siqveland | 32/26 |
| 2,419,045 A | 4/1947 | Whittaker | 128/305 |
| 2,773,501 A | 12/1956 | Young | 128/221 |
| 3,104,448 A | 9/1963 | Morrow et al. | |
| 3,120,845 A | 2/1964 | Horner | 128/310 |
| 3,173,417 A | 3/1965 | Horner | 128/305 |
| 3,175,554 A | 3/1965 | Stewart | 128/2 |
| 3,507,276 A | 4/1970 | Burgess et al. | 128/173 |
| 3,543,966 A | 12/1970 | Ryan et al. | 222/94 |
| 3,815,605 A | 6/1974 | Schmidt et al. | 128/305 |
| 3,835,860 A | 9/1974 | Garretson et al. | 128/310 |
| 3,893,445 A | 7/1975 | Hofsess | 128/2 B |
| 3,991,765 A | 11/1976 | Cohen | 128/305 |
| 4,021,920 A | 5/1977 | Kirschner et al. | 32/28 |

(Continued)

FOREIGN PATENT DOCUMENTS

| | | | |
|---|---|---|---|
| CA | 2138842 | 6/1996 | A61M 19/00 |
| CA | 2 454 600 | 1/2004 | |

(Continued)

OTHER PUBLICATIONS

International PCT Search Report PCT/US03/17167, 8 pages.

(Continued)

*Primary Examiner* — Max Hindenburg
*Assistant Examiner* — Renee Danega
(74) *Attorney, Agent, or Firm* — Fulbright & Jaworski, LLP

(57) ABSTRACT

An apparatus and method for harvesting bone and bone marrow are provided. The apparatus may include a driver operable to be releasably engaged with an intraosseous device. The intraosseous device may include a cannula having a first end operable to penetrate bone and bone marrow and to allow retrieval of portions of bone and/or bone marrow. The cannula may have a second end operable to be releasably engaged with bone marrow sampling equipment. The apparatus may include a removable trocar. The removable trocar may have an inner channel operable to convey portions of bone and/or bone marrow. The removable trocar may have an inner channel and a side port communicating with the inner channel. The removable trocar may have a first end operable to penetrate bone and bone marrow.

15 Claims, 6 Drawing Sheets

(56) References Cited

U.S. PATENT DOCUMENTS

| | | | |
|---|---|---|---|
| 4,099,518 A | 7/1978 | Baylis et al. | 600/567 |
| 4,124,026 A | 11/1978 | Berner et al. | 606/104 |
| 4,142,517 A | 3/1979 | Stavropoulos et al. | 128/2 B |
| 4,170,993 A | 10/1979 | Alvarez | 128/214 R |
| 4,185,619 A | 1/1980 | Reiss | 128/1.1 |
| 4,194,505 A | 3/1980 | Schmitz | 604/138 |
| 4,258,722 A | 3/1981 | Sessions et al. | 128/753 |
| 4,262,676 A | 4/1981 | Jamshidi | 128/753 |
| 4,306,570 A | 12/1981 | Matthews | 128/754 |
| 4,333,459 A | 6/1982 | Becker | 128/218 |
| 4,381,777 A | 5/1983 | Garnier | 604/188 |
| 4,441,563 A | 4/1984 | Walton, II | 173/163 |
| 4,469,109 A | 9/1984 | Mehl | 128/753 |
| 4,484,577 A | 11/1984 | Sackner et al. | 128/203.28 |
| 4,543,966 A | 10/1985 | Islam et al. | 128/754 |
| 4,553,539 A | 11/1985 | Morris | 128/132 D |
| 4,605,011 A | 8/1986 | Naslund | 128/752 |
| 4,620,539 A | 11/1986 | Andrews et al. | 128/303 |
| 4,646,731 A | 3/1987 | Brower | 128/156 |
| 4,654,492 A | 3/1987 | Koerner et al. | 200/153 P |
| 4,655,226 A | 4/1987 | Lee | 128/754 |
| 4,659,329 A | 4/1987 | Annis | 604/180 |
| 4,692,073 A | 9/1987 | Martindell | |
| 4,711,636 A | 12/1987 | Bierman | 604/180 |
| 4,713,061 A | 12/1987 | Tarello et al. | 604/200 |
| 4,716,901 A | 1/1988 | Jackson et al. | 128/343 |
| 4,723,945 A | 2/1988 | Theiling | 604/232 |
| 4,758,225 A | 7/1988 | Cox et al. | 604/126 |
| 4,762,118 A | 8/1988 | Lia et al. | 128/4 |
| 4,772,261 A | 9/1988 | Von Hoff et al. | 604/51 |
| 4,787,893 A | 11/1988 | Villette | 604/188 |
| 4,793,363 A | 12/1988 | Ausherman et al. | 128/754 |
| 4,867,158 A | 9/1989 | Sugg | 128/305 |
| 4,919,146 A | 4/1990 | Rhinehart et al. | 128/752 |
| 4,921,013 A | 5/1990 | Spalink et al. | 137/614.05 |
| 4,935,010 A | 6/1990 | Cox et al. | 604/122 |
| 4,940,459 A | 7/1990 | Noce | 604/98 |
| 4,944,677 A | 7/1990 | Alexandre | 433/165 |
| 4,969,870 A | 11/1990 | Kramer et al. | 604/51 |
| 4,986,279 A | 1/1991 | O'Neill | 128/754 |
| 5,002,546 A | 3/1991 | Romano | 606/80 |
| 5,025,797 A | 6/1991 | Baran | 128/754 |
| 5,036,860 A | 8/1991 | Leigh et al. | 128/754 |
| 5,057,085 A | 10/1991 | Kopans | 604/173 |
| 5,074,311 A | 12/1991 | Hasson | 128/754 |
| 5,116,324 A | 5/1992 | Brierley et al. | 604/180 |
| 5,120,312 A | 6/1992 | Wigness et al. | 604/175 |
| 5,122,114 A | 6/1992 | Miller et al. | 604/49 |
| 5,133,359 A | 7/1992 | Kedem | 128/754 |
| 5,137,518 A | 8/1992 | Mersch | 604/168 |
| 5,139,500 A | 8/1992 | Schwartz | 606/96 |
| RE34,056 E | 9/1992 | Lindgren et al. | 128/754 |
| 5,172,701 A | 12/1992 | Leigh et al. | 128/753 |
| 5,172,702 A | 12/1992 | Leigh et al. | 128/754 |
| 5,176,643 A | 1/1993 | Kramer et al. | 604/135 |
| 5,195,985 A | 3/1993 | Hall | 604/195 |
| 5,203,056 A | 4/1993 | Funk et al. | 24/543 |
| 5,207,697 A | 5/1993 | Carusillo et al. | 606/167 |
| 5,249,583 A | 10/1993 | Mallaby | 128/754 |
| 5,257,632 A | 11/1993 | Turkel et al. | 128/754 |
| 5,261,877 A | 11/1993 | Fine et al. | 604/540 |
| 5,269,785 A | 12/1993 | Bonutti | 606/80 |
| 5,279,306 A | 1/1994 | Mehl | 128/753 |
| 5,312,351 A | 5/1994 | Gerrone | 604/117 |
| 5,312,364 A | 5/1994 | Jacobs | 604/180 |
| 5,312,408 A | 5/1994 | Brown | 606/80 |
| 5,324,300 A * | 6/1994 | Elias et al. | 606/180 |
| 5,332,398 A | 7/1994 | Miller et al. | 604/181 |
| 5,333,790 A | 8/1994 | Christopher | 239/391 |
| 5,341,823 A | 8/1994 | Manosalva et al. | 128/898 |
| 5,348,022 A | 9/1994 | Leigh et al. | 128/753 |
| 5,357,974 A | 10/1994 | Baldridge | 128/754 |
| 5,368,046 A | 11/1994 | Scarfone et al. | 128/754 |
| 5,372,583 A | 12/1994 | Roberts et al. | 604/51 |
| 5,383,859 A | 1/1995 | Sewell, Jr. | 604/164 |
| 5,385,553 A | 1/1995 | Hart et al. | 604/167 |
| 5,400,798 A | 3/1995 | Baran | 128/754 |
| 5,405,348 A | 4/1995 | Anspach. et al. | 606/80 |
| 5,423,824 A | 6/1995 | Akerfeldt et al. | 606/80 |
| 5,431,655 A | 7/1995 | Melker et al. | 606/79 |
| 5,451,210 A | 9/1995 | Kramer et al. | 604/137 |
| 5,484,442 A | 1/1996 | Melker et al. | 606/79 |
| D369,858 S | 5/1996 | Baker et al. | D24/112 |
| 5,526,821 A | 6/1996 | Jamshidi | 128/753 |
| 5,529,580 A | 6/1996 | Kusunoki et al. | 606/170 |
| 5,549,565 A | 8/1996 | Ryan et al. | 604/167 |
| 5,554,154 A | 9/1996 | Rosenberg | 606/80 |
| 5,556,399 A | 9/1996 | Huebner | 606/80 |
| 5,558,737 A | 9/1996 | Brown et al. | 156/172 |
| 5,571,133 A | 11/1996 | Yoon | 606/185 |
| 5,586,847 A | 12/1996 | Mattern, Jr. et al. | 408/239 A |
| 5,591,188 A | 1/1997 | Waisman | 606/182 |
| 5,595,186 A | 1/1997 | Rubinstein et al. | 600/567 |
| 5,601,559 A | 2/1997 | Melker et al. | 606/79 |
| 5,632,747 A | 5/1997 | Scarborough et al. | 606/79 |
| 5,672,155 A | 9/1997 | Riley et al. | 604/154 |
| 5,713,368 A | 2/1998 | Leigh | 128/753 |
| 5,724,873 A | 3/1998 | Hillinger | 81/451 |
| 5,733,262 A | 3/1998 | Paul | 604/116 |
| 5,752,923 A | 5/1998 | Terwilliger | 600/562 |
| 5,762,639 A | 6/1998 | Gibbs | 604/272 |
| 5,766,221 A | 6/1998 | Benderev et al. | 606/232 |
| 5,769,086 A | 6/1998 | Ritchart et al. | 128/753 |
| 5,779,708 A | 7/1998 | Wu | 606/80 |
| 5,800,389 A | 9/1998 | Burney et al. | 604/93 |
| 5,807,277 A | 9/1998 | Swaim | 600/567 |
| 5,810,826 A | 9/1998 | Akerfeldt et al. | 606/80 |
| 5,817,052 A | 10/1998 | Johnson et al. | 604/51 |
| 5,823,970 A | 10/1998 | Terwilliger | 600/564 |
| D403,405 S | 12/1998 | Terwilliger | D24/130 |
| 5,858,005 A | 1/1999 | Kriesel | 604/180 |
| 5,868,711 A | 2/1999 | Kramer et al. | 604/136 |
| 5,868,750 A | 2/1999 | Schultz | 606/104 |
| 5,873,510 A | 2/1999 | Hirai et al. | 227/130 |
| 5,885,226 A | 3/1999 | Rubinstein et al. | 600/564 |
| 5,891,085 A | 4/1999 | Lilley et al. | 604/68 |
| 5,911,701 A | 6/1999 | Miller et al. | 604/22 |
| 5,911,708 A | 6/1999 | Teirstein | 604/183 |
| 5,916,229 A | 6/1999 | Evans | 606/171 |
| 5,919,172 A | 7/1999 | Golba, Jr. | 604/272 |
| 5,924,864 A | 7/1999 | Loge et al. | 433/118 |
| 5,927,976 A | 7/1999 | Wu | 433/82 |
| 5,928,238 A | 7/1999 | Scarborough et al. | 606/79 |
| 5,941,706 A | 8/1999 | Ura | 433/165 |
| 5,941,851 A | 8/1999 | Coffey et al. | 604/131 |
| 5,960,797 A | 10/1999 | Kramer et al. | 128/899 |
| 5,980,545 A | 11/1999 | Pacala et al. | 606/170 |
| 5,993,417 A | 11/1999 | Yerfino et al. | 604/110 |
| 5,993,454 A | 11/1999 | Longo | 606/80 |
| 6,007,496 A | 12/1999 | Brannon | 600/565 |
| 6,017,348 A | 1/2000 | Hart et al. | 606/79 |
| 6,018,094 A | 1/2000 | Fox | 623/11 |
| 6,022,324 A | 2/2000 | Skinner | 600/566 |
| 6,027,458 A | 2/2000 | Janssens | 600/567 |
| 6,033,369 A | 3/2000 | Goldenberg | 600/567 |
| 6,033,411 A | 3/2000 | Preissman | 606/99 |
| 6,063,037 A | 5/2000 | Mittermeier et al. | 600/567 |
| 6,071,284 A | 6/2000 | Fox | 606/80 |
| 6,080,115 A | 6/2000 | Rubinstein | 600/567 |
| 6,083,176 A | 7/2000 | Terwilliger | 600/562 |
| 6,086,543 A | 7/2000 | Anderson et al. | 600/567 |
| 6,086,544 A | 7/2000 | Hibner et al. | 600/568 |
| 6,096,042 A | 8/2000 | Herbert | 606/80 |
| 6,102,915 A | 8/2000 | Bresler et al. | 606/80 |
| 6,106,484 A | 8/2000 | Terwilliger | 600/568 |
| 6,110,128 A | 8/2000 | Andelin et al. | 600/566 |
| 6,110,129 A | 8/2000 | Terwilliger | 600/567 |
| 6,110,174 A | 8/2000 | Nichter | 606/72 |
| 6,120,462 A * | 9/2000 | Hibner et al. | 600/566 |
| 6,135,769 A | 10/2000 | Kwan | 433/80 |
| 6,159,163 A | 12/2000 | Strauss et al. | 600/566 |
| 6,162,203 A | 12/2000 | Haaga | 604/272 |
| 6,183,442 B1 | 2/2001 | Athanasiou et al. | 604/154 |
| 6,210,376 B1 | 4/2001 | Grayson | 604/264 |

(56) References Cited

U.S. PATENT DOCUMENTS

| | | | |
|---|---|---|---|
| 6,217,561 B1 | 4/2001 | Gibbs | 604/264 |
| 6,221,029 B1 | 4/2001 | Mathis et al. | 600/564 |
| 6,228,049 B1 | 5/2001 | Schroeder et al. | 604/93.01 |
| 6,228,088 B1 | 5/2001 | Miller et al. | 606/80 |
| 6,238,355 B1 | 5/2001 | Daum | 600/567 |
| 6,247,928 B1 | 6/2001 | Meller et al. | 433/80 |
| 6,248,110 B1 | 6/2001 | Reiley et al. | 606/93 |
| 6,257,351 B1 | 7/2001 | Ark et al. | 173/178 |
| 6,267,763 B1 | 7/2001 | Castro | 606/86 A |
| 6,273,715 B1 | 8/2001 | Meller et al. | 433/80 |
| 6,273,862 B1 | 8/2001 | Privitera et al. | 600/568 |
| 6,283,925 B1 | 9/2001 | Terwilliger | 600/568 |
| 6,283,970 B1 | 9/2001 | Lubinus | 606/80 |
| 6,287,114 B1 | 9/2001 | Meller et al. | 433/80 |
| 6,302,852 B1 | 10/2001 | Fleming, III et al. | 600/567 |
| 6,309,358 B1 | 10/2001 | Okubo | 600/466 |
| 6,312,394 B1 | 11/2001 | Fleming, III | 600/567 |
| 6,315,737 B1 | 11/2001 | Skinner | 600/566 |
| 6,325,806 B1 | 12/2001 | Fox | 606/80 |
| 6,328,701 B1 | 12/2001 | Terwilliger | 600/567 |
| 6,328,744 B1 | 12/2001 | Harari et al. | 606/80 |
| 6,358,252 B1 | 3/2002 | Shapira | 606/80 |
| 6,402,701 B1 | 6/2002 | Kaplan et al. | 600/567 |
| 6,419,490 B1 | 7/2002 | Kitchings Weathers, Jr. | 433/165 |
| 6,425,888 B1 | 7/2002 | Embleton et al. | 604/290 |
| 6,428,487 B1 | 8/2002 | Burdorff et al. | 600/568 |
| 6,443,910 B1 | 9/2002 | Krueger et al. | 600/567 |
| 6,458,117 B1 | 10/2002 | Pollins, Sr. | 604/523 |
| 6,468,248 B1 | 10/2002 | Gibbs | 604/164.01 |
| 6,478,751 B1 | 11/2002 | Krueger et al. | 600/566 |
| 6,488,636 B2 | 12/2002 | Bryan et al. | 600/565 |
| 6,523,698 B1 | 2/2003 | Dennehey et al. | 210/435 |
| 6,527,736 B1 | 3/2003 | Attinger et al. | 604/43 |
| 6,527,778 B2 | 3/2003 | Athanasiou et al. | 606/80 |
| 6,540,694 B1 | 4/2003 | Van Bladel et al. | 600/564 |
| 6,547,511 B1 | 4/2003 | Adams | 414/46.4 |
| 6,547,561 B2 | 4/2003 | Meller et al. | 433/32 |
| 6,554,779 B2 | 4/2003 | Viola et al. | 600/568 |
| 6,555,212 B2 | 4/2003 | Boiocchi et al. | 428/295.4 |
| 6,582,399 B1 | 6/2003 | Smith et al. | 604/152 |
| 6,585,622 B1 | 7/2003 | Shum et al. | 482/8 |
| 6,595,911 B2 | 7/2003 | LoVuolo | 600/30 |
| 6,595,979 B1 | 7/2003 | Epstein et al. | 604/506 |
| 6,613,054 B2 | 9/2003 | Scribner et al. | 606/93 |
| 6,616,632 B2 | 9/2003 | Sharp et al. | 604/117 |
| 6,620,111 B2 | 9/2003 | Stephens et al. | 600/567 |
| 6,626,848 B2 | 9/2003 | Neuenfeldt | 600/564 |
| 6,626,887 B1 | 9/2003 | Wu | 604/512 |
| 6,638,235 B2 | 10/2003 | Miller et al. | 600/566 |
| 6,656,133 B2 | 12/2003 | Voegele et al. | 600/568 |
| 6,689,072 B2 | 2/2004 | Kaplan et al. | 600/567 |
| 6,702,760 B2 | 3/2004 | Krause et al. | 600/564 |
| 6,702,761 B1 | 3/2004 | Damadian et al. | 600/576 |
| 6,706,016 B2 | 3/2004 | Cory et al. | 604/117 |
| 6,716,192 B1 | 4/2004 | Orosz, Jr. | 604/117 |
| 6,716,215 B1 | 4/2004 | David et al. | 606/80 |
| 6,716,216 B1 | 4/2004 | Boucher et al. | 606/86 |
| 6,730,043 B2 | 5/2004 | Krueger et al. | 600/567 |
| 6,730,044 B2 | 5/2004 | Stephens et al. | 600/568 |
| 6,749,576 B2 | 6/2004 | Bauer | 600/567 |
| 6,752,768 B2 | 6/2004 | Burdorff et al. | 600/568 |
| 6,752,816 B2 | 6/2004 | Culp et al. | 606/170 |
| 6,758,824 B1 | 7/2004 | Miller et al. | 600/568 |
| 6,761,726 B1 | 7/2004 | Findlay et al. | 606/182 |
| 6,796,957 B2 | 9/2004 | Carpenter et al. | 604/93.01 |
| 6,846,314 B2 | 1/2005 | Shapira | 606/80 |
| 6,849,051 B2 * | 2/2005 | Sramek et al. | 600/565 |
| 6,855,148 B2 | 2/2005 | Foley et al. | 606/86 |
| 6,860,860 B2 | 3/2005 | Viola | 600/564 |
| 6,875,183 B2 | 4/2005 | Cervi | 600/567 |
| 6,875,219 B2 | 4/2005 | Arramon et al. | 606/92 |
| 6,884,245 B2 | 4/2005 | Spranza | 606/79 |
| 6,887,209 B2 | 5/2005 | Kadziauskas et al. | 600/565 |
| 6,890,308 B2 | 5/2005 | Islam | 600/564 |
| 6,902,559 B2 | 6/2005 | Taufig | 604/542 |
| 6,905,486 B2 | 6/2005 | Gibbs | 604/264 |
| 6,916,292 B2 * | 7/2005 | Morawski et al. | 600/567 |
| 6,930,461 B2 | 8/2005 | Rutkowski | 318/567 |
| 6,942,669 B2 | 9/2005 | Kurc | 606/80 |
| 6,969,373 B2 * | 11/2005 | Schwartz et al. | 604/170.03 |
| 7,008,381 B2 | 3/2006 | Janssens | 600/564 |
| 7,008,383 B1 | 3/2006 | Damadian et al. | 600/567 |
| 7,008,394 B2 | 3/2006 | Geise et al. | 615/6.15 |
| 7,025,732 B2 | 4/2006 | Thompson et al. | 600/654 |
| 7,063,672 B2 | 6/2006 | Schramm | 600/564 |
| 7,137,985 B2 | 11/2006 | Jahng | 606/61 |
| 7,186,257 B2 | 3/2007 | Kim | 606/96 |
| 7,207,949 B2 | 4/2007 | Miles et al. | 600/554 |
| 7,226,450 B2 | 6/2007 | Athanasiou et al. | 606/80 |
| 7,229,401 B2 | 6/2007 | Kindlein | 600/7 |
| 7,670,328 B2 | 3/2010 | Miller | 604/506 |
| 7,699,850 B2 | 4/2010 | Miller | 606/80 |
| 7,811,260 B2 | 10/2010 | Miller et al. | 604/188 |
| 7,815,642 B2 | 10/2010 | Miller | 606/79 |
| 7,850,620 B2 | 12/2010 | Miller et al. | 600/568 |
| 7,899,528 B2 | 3/2011 | Miller et al. | 607/3 |
| 7,951,089 B2 | 5/2011 | Miller | 600/566 |
| 8,038,664 B2 | 10/2011 | Miller et al. | 604/506 |
| 8,308,693 B2 | 11/2012 | Miller et al. | 604/188 |
| 8,419,683 B2 | 4/2013 | Miller et al. | 604/117 |
| 8,506,568 B2 | 8/2013 | Miller | 606/80 |
| 2001/0005778 A1 | 6/2001 | Ouchi | 600/564 |
| 2001/0014439 A1 | 8/2001 | Meller et al. | 433/50 |
| 2001/0047183 A1 | 11/2001 | Privitera et al. | 606/170 |
| 2001/0053888 A1 | 12/2001 | Athanasiou et al. | 604/154 |
| 2002/0042581 A1 | 4/2002 | Cervi | 600/567 |
| 2002/0055713 A1 | 5/2002 | Gibbs | 604/164.01 |
| 2002/0120212 A1 | 8/2002 | Ritchart et al. | 600/567 |
| 2002/0138021 A1 | 9/2002 | Pflueger | 600/565 |
| 2002/0151902 A1 | 10/2002 | Riedel | 606/79 |
| 2003/0028146 A1 | 2/2003 | Aves | 604/164.06 |
| 2003/0032939 A1 | 2/2003 | Gibbs | 604/510 |
| 2003/0036747 A1 | 2/2003 | Ie et al. | 606/1 |
| 2003/0050574 A1 | 3/2003 | Krueger | 600/567 |
| 2003/0114858 A1 | 6/2003 | Athanasiou et al. | 606/80 |
| 2003/0125639 A1 | 7/2003 | Fisher et al. | 600/564 |
| 2003/0153842 A1 | 8/2003 | Lamoureux et al. | 600/564 |
| 2003/0191414 A1 | 10/2003 | Reiley et al. | 600/567 |
| 2003/0195436 A1 | 10/2003 | Van Bladel et al. | 600/584 |
| 2003/0195524 A1 | 10/2003 | Barner | 606/119 |
| 2003/0199787 A1 | 10/2003 | Schwindt | 600/568 |
| 2003/0216667 A1 | 11/2003 | Viola | 600/564 |
| 2003/0225344 A1 | 12/2003 | Miller | 600/568 |
| 2003/0225364 A1 | 12/2003 | Kraft et al. | 604/35 |
| 2003/0225411 A1 | 12/2003 | Miller | 606/80 |
| 2004/0019297 A1 | 1/2004 | Angel | 600/564 |
| 2004/0019299 A1 | 1/2004 | Ritchart et al. | 600/567 |
| 2004/0034280 A1 | 2/2004 | Privitera et al. | 600/170 |
| 2004/0049128 A1 | 3/2004 | Miller et al. | 600/566 |
| 2004/0064136 A1 | 4/2004 | Papineau et al. | 606/41 |
| 2004/0073139 A1 | 4/2004 | Hirsch et al. | 600/564 |
| 2004/0092946 A1 | 5/2004 | Bagga et al. | 606/93 |
| 2004/0153003 A1 | 8/2004 | Cicenas et al. | 600/564 |
| 2004/0158172 A1 | 8/2004 | Hancock | 600/564 |
| 2004/0158173 A1 | 8/2004 | Voegele et al. | 600/568 |
| 2004/0162505 A1 | 8/2004 | Kaplan et al. | 600/567 |
| 2004/0191897 A1 | 9/2004 | Muschler | 435/325 |
| 2004/0210161 A1 | 10/2004 | Burdorff et al. | 600/566 |
| 2004/0215102 A1 | 10/2004 | Ikehara et al. | 600/562 |
| 2004/0220497 A1 | 11/2004 | Findlay et al. | 600/562 |
| 2005/0027210 A1 | 2/2005 | Miller | 600/567 |
| 2005/0040060 A1 | 2/2005 | Andersen et al. | 206/363 |
| 2005/0075581 A1 | 4/2005 | Schwindt | 600/568 |
| 2005/0085838 A1 | 4/2005 | Thompson et al. | 606/170 |
| 2005/0101880 A1 | 5/2005 | Cicenas et al. | 600/567 |
| 2005/0113716 A1 | 5/2005 | Mueller, Jr. et al. | 600/568 |
| 2005/0124915 A1 | 6/2005 | Eggers et al. | 600/568 |
| 2005/0131345 A1 | 6/2005 | Miller | 604/117 |
| 2005/0148940 A1 | 7/2005 | Miller | 604/187 |
| 2005/0165328 A1 | 7/2005 | Heske et al. | 600/566 |
| 2005/0165403 A1 | 7/2005 | Miller | 606/79 |
| 2005/0165404 A1 | 7/2005 | Miller | 606/80 |
| 2005/0171504 A1 | 8/2005 | Miller | 604/506 |
| 2005/0182394 A1 | 8/2005 | Spero | 606/23 |

(56) References Cited

U.S. PATENT DOCUMENTS

| | | | |
|---|---|---|---|
| 2005/0200087 A1 | 9/2005 | Vasudeva et al. | 279/143 |
| 2005/0203439 A1 | 9/2005 | Heske et al. | 600/566 |
| 2005/0209530 A1 | 9/2005 | Pflueger | 600/567 |
| 2005/0215921 A1 | 9/2005 | Hibner et al. | 600/566 |
| 2005/0228309 A1 | 10/2005 | Fisher et al. | 600/562 |
| 2005/0261693 A1 | 11/2005 | Miller et al. | 606/80 |
| 2006/0011506 A1 | 1/2006 | Riley | 206/570 |
| 2006/0015066 A1 | 1/2006 | Turieo et al. | 604/136 |
| 2006/0036212 A1 | 2/2006 | Miller | 604/48 |
| 2006/0052790 A1 | 3/2006 | Miller | 606/80 |
| 2006/0074345 A1 | 4/2006 | Hibner | 600/566 |
| 2006/0079774 A1 | 4/2006 | Anderson | 600/442 |
| 2006/0089565 A1 | 4/2006 | Schramm | 600/568 |
| 2006/0122535 A1 | 6/2006 | Daum | 600/565 |
| 2006/0129082 A1 | 6/2006 | Rozga | 604/6.04 |
| 2006/0144548 A1 | 7/2006 | Beckman et al. | 163/1 |
| 2006/0149163 A1 | 7/2006 | Hibner et al. | 600/566 |
| 2006/0167377 A1 | 7/2006 | Ritchart et al. | 600/566 |
| 2006/0167378 A1 | 7/2006 | Miller | 600/566 |
| 2006/0167379 A1 | 7/2006 | Miller | 600/566 |
| 2006/0184063 A1 | 8/2006 | Miller | 600/568 |
| 2006/0189940 A1 | 8/2006 | Kirsch | 604/164.1 |
| 2007/0016100 A1 | 1/2007 | Miller | 600/567 |
| 2007/0049945 A1 | 3/2007 | Miller | 606/86 |
| 2007/0149920 A1 | 6/2007 | Michels et al. | 604/93.01 |
| 2007/0213735 A1 | 9/2007 | Saadat et al. | 606/79 |
| 2007/0270775 A1 | 11/2007 | Miller et al. | 604/506 |
| 2008/0015467 A1 | 1/2008 | Miller | 600/568 |
| 2008/0015468 A1 | 1/2008 | Miller | 600/568 |
| 2008/0045857 A1 | 2/2008 | Miller | 600/566 |
| 2008/0045860 A1 | 2/2008 | Miller et al. | 600/567 |
| 2008/0045861 A1 | 2/2008 | Miller et al. | 600/567 |
| 2008/0045965 A1 | 2/2008 | Miller et al. | 606/80 |
| 2008/0140014 A1 | 6/2008 | Miller et al. | 604/180 |
| 2008/0215056 A1 | 9/2008 | Miller et al. | 606/80 |
| 2008/0221580 A1 | 9/2008 | Miller et al. | 606/80 |

FOREIGN PATENT DOCUMENTS

| | | | |
|---|---|---|---|
| CN | 2320209 | 5/1999 | |
| CN | 2664675 | 12/2004 | |
| DE | 10057931 A1 | 11/2000 | A61B 17/32 |
| EP | 517000 | 12/1992 | A61M 5/168 |
| EP | 0807412 A1 | 11/1997 | A61B 17/32 |
| EP | 1099450 | 5/2001 | A61M 5/32 |
| EP | 1314452 | 5/2003 | |
| FR | 853349 | 3/1940 | |
| FR | 2457105 | 5/1979 | |
| FR | 2516386 | 11/1981 | |
| GB | 2130890 A | 6/1984 | |
| JP | 1052433 | 2/1989 | A61B 1/00 |
| WO | WO 9208410 | 5/1992 | |
| WO | 93/07819 | 4/1993 | A61B 17/32 |
| WO | 96/31164 | 10/1996 | A61B 17/34 |
| WO | 98/06337 | 2/1998 | A61B 17/16 |
| WO | 99/18866 | 4/1999 | A61B 17/34 |
| WO | 99/52444 | 10/1999 | A61B 17/00 |
| WO | 00/56220 | 9/2000 | A61B 10/00 |
| WO | 01/78590 | 10/2001 | A61B 5/00 |
| WO | 02/41792 A1 | 5/2002 | A61B 17/16 |
| WO | 0241792 | 5/2002 | A61B 17/16 |
| WO | 0296497 | 12/2002 | A61M 31/00 |
| WO | 2005072625 A2 | 8/2005 | A61M 17/00 |
| WO | 2005110259 | 11/2005 | A61B 17/88 |
| WO | 2005112800 | 12/2005 | A61B 17/34 |
| WO | 2008081438 | 7/2008 | |

OTHER PUBLICATIONS

International PCT Search Report PCT/US03/17203, 8 pages.
International PCT Search Report PCT/US2004/037753, 6 pages.
Communication relating to the results of the partial International Search Report for PCT/US2005/002484, 6 pages.
International PCT Search Report and Written Opinion PCT/US2004/037753, 16 pages.
International PCT Search Report and Written Opinion PCTrUS2005/002484, 15 pp.
Cummins, Richard O., et al, "ACLS-Principles and Practice", ACLS—The Reference Textbook, American Heart Association, pp. 214-218.
Riley et al., "A Pathologist's Perspective on Bone Marrow Aspiration Biopsy: I. Performing a Bone Marrow Examination," Journal of Clinical Laboratory Analysis 18, pp. 70-90.
International Preliminary Report on Patentability PCT/US2005/002484, 9 pages.
Official Action for European Application No. 03756317.8 (4 pages).
International Search Report and Written Opinion for International Application No. PCT/US2006/025201 (18 pages).
Pediatrics, Official Journal of the American Academy of Pediatrics, Pediatrics, 2005 American Heart Association Guidelines for Cardiopulmonary Resuscitation and Emergency Cardiovascular Care of Pediatric and Neonatal Patients:Pediatric Advanced Life Support, Downloaded from www.pediatrics.org.
Liakat a. Parapia, Trepanning or trephines: a history of bone marrow biopsy, British Journal of Haematology, pp. 14-19 2007.
Australian Exam Report on Patent Application No. 2003240970, 2 pages, Oct. 15, 2007.
Pediatric Emergency, Intraosseous Infusion for Administration of Fluids and Drugs, www.cookgroup.com, 1 pg.
Michael Trotty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages.
Buckley et al., CT-guided bone biopsy: Initial experience with commercially available hand held Black and Decker drill, European Journal of Radiology 61, pp. 176-180.
Hakan et al., CT-guided Bone BiopsyPerformed by Means of Coaxial Bopsy System with an Eccentric Drill, Radiology, pp. 549-552.
European Search Report 08158699.2-1265, 4 pages.
International Search Report and Written Opinion, PCT/US2007/078204, 14 pages.
International Search Report and Written Opinion, PCT/US08/52943 8 pages.
European Office Action Communication, Application No. 08158699. 2-1265/1967142, 10 pages.
Gunal et al., Compartment Syndrome After Intraosseous Infusion: An Expiremental Study in Dogs, Journal of Pediatric Surgery, vol. 31, No. 11, pp. 1491-1493.
International Search Report, PCT/US2007/072217, 20 pages.
International Search Report, PCT/US2007/072209, 18 pages.
International Search Report, PCT/US2006/025201, 12 pages.
Communication Pursuant to Article 94(3) EPC, Application No. 05 712 091.7-1265, 4 pages.
Notification of the First Chinese Office Action, Application No. 200580003261.8, 3 pages.
International Search Report and Written Opinion, PCT/US08/500346, 12 pages.
PCT Invitation to Pay Additional Fees, PCT/US2007/072209, 9 pages.
"Proven reliability for quality bone marrow samples", Special Procedures, Cardinal Health, 6 pages.
F.A.S.T. 1 Intraosseous Infusion System with Depth-Control Mechanism Brochure, 6 pages.
BioAccess.com, Single Use Small Bone Power Tool—How It Works, 1 pg.
International Search Report and Written Opinion, PCT/US2007/078203, 15 pages.
International Search Report and Written Opinion, PCT/US2007/072202, 17 pages.
International Search Report and Written Opinion, PCT/US2007/078207, 13 pages.
International Search Report and Written Opinion, PCT/US2007/078205, 13 pages.
European Office Action EP03731475.4, 4 pages.
U.S. Appl. No. 11/427,501 Non Final Office Action, 14 pages.
Non-Final Office Action, U.S. Appl. No. 10/449,476, 8 pages.

(56) References Cited

OTHER PUBLICATIONS

International Preliminary Report on Patentability, PCT/US2007/072202, 10 pages.
International Preliminary Report on Patentability, PCT/US2007/072217, 11 pages.
Astrom, K.G., "Automatic Biopsy Instruments Used Through a Coaxial Bone Biopsy System with an Eccentric Drill Tip," Acta Radiologica, 1995; 36:237-242.
Astrom, K. Gunnar 0., "CT-guided Transsternal Core Biopsy of Anterior Mediastinal Masses," Radiology 1996; 199:564-567.
Chinese Office Action, Application No. 2005800003261, (with English translation), (9 pgs).
International Preliminary Report on Patentability, PCT/US/2007/078203, 13 pages.
International Preliminary Report on Patentability, PCT/US/2007/078207, 10 pages.
International Preliminary Report on Patentability, PCT/US/2007/078205, 10 pages.
International Preliminary Report on Patentability, PCT/US/2007/078204, 11 pages.
Vidacare Corporation Comments to Intraosseous Vascular Access Position Paper, Infusion Nurses Society, 6 pages.
International Preliminary Report on Patentability, PCT/US/2007/072209, 10 pages.
Japanese Office Action, Application No. 2004-508,670, (with English summary), (13 pgs).
PCT Preliminary Report on Patentability, PCT/US/2008/050346, (8 pgs).
Japanese Office Action, Application No. 2004-508,669, (with English summary), (9 pgs).
Chinese Office Action, Application No. 200780000590.6, (with English translation), (13 pgs).
European Office Action and Search Report, Application No. 09150973.7, (8 pgs).
International Preliminary Report on Patentability, PCT/US08/52943, 7 pages.
Chinese Office Action w/english translation; Application No. 200680021872.X; Pgs. 8.
European Extended Search Report, Application No. EP08021732.6, 7 pages.
European Office Action; Application No. 09 155 111.9 - 2310; Pgs. 3.
Chinese Office Action with English translation; Application No. 200910006631.3; Pgs. 12, Mar. 11, 2010.
European Extended Search Report, Application No. EP10153350.3, 5 pages.
Taiwan Office Action , Application No. 94102179 (with English translation); 12 pages.
Chinese Office Action with English translation; Application No. 200780001198.3; Pgs. 13.
Chinese Office Action with English translation; Application No. 200780001190.7; 12 pgs.
Chinese Office Action with English translation; Application No. 200780001196; 12 pgs.

\* cited by examiner

APPARATUS AND METHOD TO ACCESS THE BONE MARROW

RELATED APPLICATION

This application is a Continuation under 35 U.S.C. §120 of U.S. patent application Ser. No. 11/427,501, titled "Apparatus and Methods to Harvest Bone and Bone Marrow," filed Jun. 29, 2006 now U.S. Pat. No. 7,951,089.

This application makes cross-reference to the following related applications:

U.S. patent application Ser. No. 11/781,597, filed Jul. 23, 2007;
U.S. patent application Ser. No. 11/781,568, filed Jul. 23, 2007;
U.S. patent application Ser. No. 11/853,685, filed Sep. 11, 2007;
U.S. patent application Ser. No. 11/853,691, filed Sep. 11, 2007; and
U.S. patent application Ser. No. 12/120,992, filed May 15, 2008.

TECHNICAL FIELD

The present disclosure is related to apparatus and methods for obtaining biopsy specimens from bone and/or associated bone marrow and obtaining larger quantities of bone and/or associated bone marrow for diagnostic purposes and/or transplantation of stem cells and/or bone marrow.

BACKGROUND OF THE DISCLOSURE

There are many clinical conditions where it is important to be able to access and retrieve bone marrow. In some cases it may be necessary to treat diseases with a bone marrow or stem cell transplant to restore functioning blood cells in the body after high-dose chemotherapy. Such conditions may include acute leukemias, brain tumors, breast cancer, Hodgkin's disease, multiple myeloma, neuroblastoma, non-Hodgkin's lymphomas, ovarian cancer, sarcoma and testicular cancer. In other cases it is necessary to access the bone marrow to obtain a sample of the marrow for diagnostic testing. These conditions may include cancer of any type and hematologic disease of any origin.

Gaining access to bone and associated bone marrow for a small biopsy specimen or aspiration of a larger quantity of bone marrow may be difficult, traumatic and occasionally dangerous, depending on the selected target area for harvesting bone and/or associated bone marrow, operator expertise and patient anatomy. Many currently available devices and techniques for gaining access to a bone and associated bone marrow may include using an intraosseous (IO) needle with a removable trocar disposed therein. Handles may be used to apply pressure to and manually rotate the IO needle and trocar as a set. Such manual IO devices often require substantial force to break through the outer cortex of a bone. Exertion of such force may cause pain to a patient and may sometimes damage the bone and/or IO device.

Excessive force when harvesting bone and/or bone marrow from the sternum of a patient may cause penetration through the sternum and potentially damage the underlying heart and/or great blood vessels. Damage may also occur when harvesting bone marrow from children with softer bone structures or any patient with bones deteriorated by disease (cancer).

Retrieving bone and bone marrow samples for diagnostic purposes may often be difficult. Occasionally a core sample of bone and/or bone marrow may not be successfully retrieved using a standard biopsy needle. Thus, multiple insertions at different sites may be necessary to obtain a satisfactory bone and/or bone marrow biopsy specimen. Risks to health care personnel may be higher because of increased handling of blood contaminated sharp instruments. Accidental needle sticks and missed target areas may further complicate procedures and increase risks to health care personnel and/or patients.

Conventional bone marrow transplant techniques may require multiple penetration sites (up to 20 per patient) in order to obtain enough bone marrow (sample size) to perform a routine bone marrow transplant. This is often a labor intensive procedure. Conventional biopsy needles are typically inserted with considerable manual force. This force may cause loss of control or operator fatigue. When the biopsy needle is in place, an associated trocar is generally removed and a syringe attached to the biopsy needle to aspirate a few cubic centimeters of bone marrow. The biopsy needle is then withdrawn. A new site is penetrated by the biopsy needle generally about a centimeter from the first site and the procedure repeated.

SUMMARY OF THE DISCLOSURE

One aspect of the present disclosures may include apparatus and methods to access bone and/of bone marrow with minimum trauma to a patient and still allow removal of sufficient amounts of bone and/or bone marrow the first time a bone is penetrated. Such apparatus may include a powered driver and an intraosseous device having an outer penetrator. The outer penetrator may have a tip or first end operable to penetrate bone and associated bone marrow. The outer penetrator may also have a longitudinal bore operable to remove a bone specimen and/or bone marrow from a target area. The outer penetrator may be used to harvest bone and/or associated bone marrow with or without an inner penetrator.

For some embodiments a removable inner penetrator may be slidably disposed within an outer penetrator. The inner penetrator may have a first end operable to penetrate bone and/or bone marrow. The inner penetrator may also have a longitudinal bore operable to remove portions of bone and/or bone marrow from a target area. For some applications the inner penetrator may be a generally solid rod or shaft. For other applications, the inner penetrator may have a longitudinal bore extending therethrough. For still other applications the inner penetrator may include a chamber or cavity formed proximate the first end.

One embodiment may include a method for harvesting bone and/or bone marrow by slidably disposing portions of an inner penetrator within a hollow, outer penetrator to form an intraosseous (IO) device. The IO device may be inserted into a bone and/or associated bone marrow using a powered driver. The inner penetrator may be removed from the hollow, outer penetrator. Suction may then be applied to the hollow, outer penetrator to retrieve portions of bone and/or bone marrow via the hollow, outer penetrator.

One method of harvesting bone and/or bone marrow in accordance with teachings of the present disclosure may include inserting a hollow, outer penetrator and an inner penetrator or first trocar into a bone and associated bone marrow. The inner penetrator may then be removed and a specimen of bone and/or bone marrow may be grasped by inserting a second trocar through the outer penetrator and into the bone marrow. The outer penetrator and the second trocar may cooperate with each other to allow opening one end of the second trocar during insertion of the second trocar into the bone marrow and to close the one end of the second trocar during retrieval of the specimen.

For some embodiments an intraosseous (IO) device may be provided to remove a relatively small specimen of bone and/or bone marrow from a target area. For other embodiments an IO device may be provided to remove relatively larger quantities of bone and/or bone marrow from a target area. Such IO devices may have multiple side ports to remove bone marrow from respective target areas corresponding with each side port.

The use of a powered driver to insert an intraosseous device into a target area to obtain a bone specimen and/or to obtain bone marrow samples may substantially reduce or eliminate many of the problems associated with manually inserted biopsy needles.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein.

DETAILED DESCRIPTION OF THE DISCLOSURE

Preferred embodiments of the disclosure and its advantages are best understood by reference to FIGS. 1-9D herein like numbers refer to same and like parts.

Figure 2:
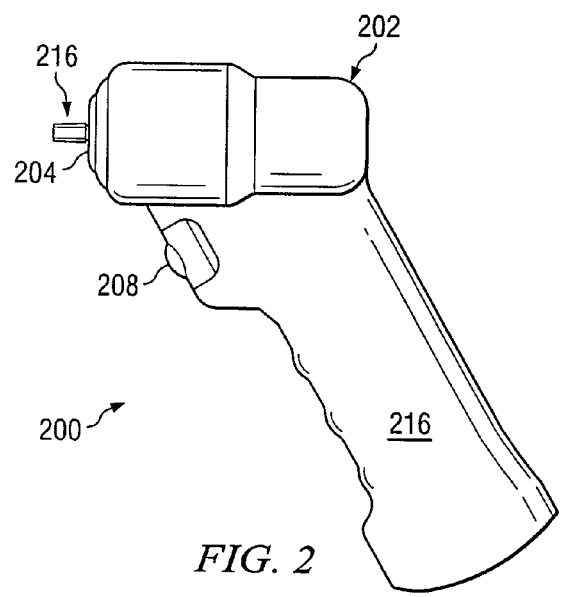
FIG. 2 is a schematic drawing showing an isometric view of one example of a powered driver which may be used to insert an intraosseous device into bone and associated bone marrow at a target area.
Figure 3:
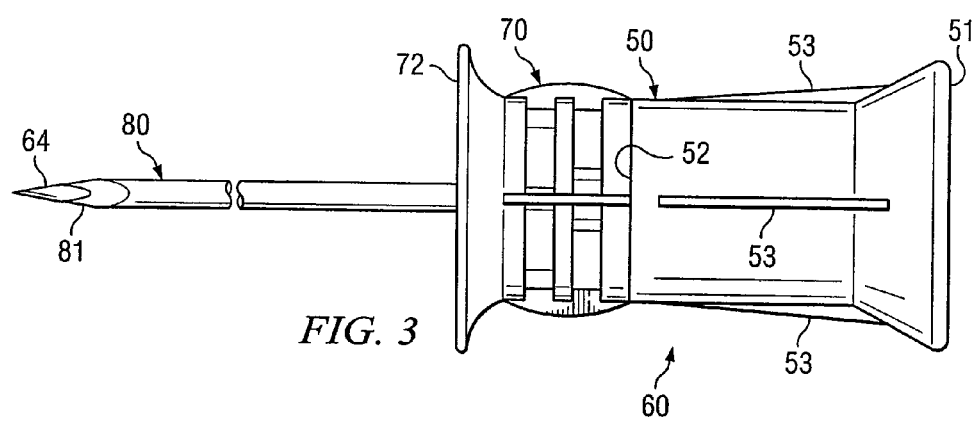
FIG. 3 is a schematic drawing showing an enlarged isometric view with portions broken away of an intraosseous device satisfactory for use in harvesting bone and/or bone marrow in accordance with teachings of the present disclosure.

The term "driver" may be used in this application to include any type of powered driver or manual driver satisfactory for installing an intraosseous (IO) device such as a penetrator assembly or an IO needle into a selected target area. Various techniques may be satisfactorily used to releasably engage or attach IO devices with powered drivers and manual drivers. Various features and steps of the present disclosure may be described with respect to powered drivers. However, various teachings of the present disclosure may also be used with manual drivers. The present disclosure is not limited to use with powered drivers such as shown in FIG. 2.

For some applications a powered driver or a manual driver may be directly coupled with an IO device. For other applications various types of connectors may be used to couple a powered driver or a manual driver with an IO device. A wide variety of connectors and associated connector receptacles, fittings and/or other types of connections with various dimensions and configurations may be satisfactorily used to releasably engage an IO device with a powered driver or a manual driver.

The term "fluid" may be used in this application to include any liquid including, but not limited to, blood, water, saline solutions, IV solutions, plasma or any mixture of liquids, particulate matter, dissolved medication and/or drugs appropriate for injection into bone marrow or other target sites. The term "fluid" may also be used in this patent application to include any body fluids and/or liquids containing particulate matter such bone marrow and/or cells which may be withdrawn from a target area.

Figure 1:
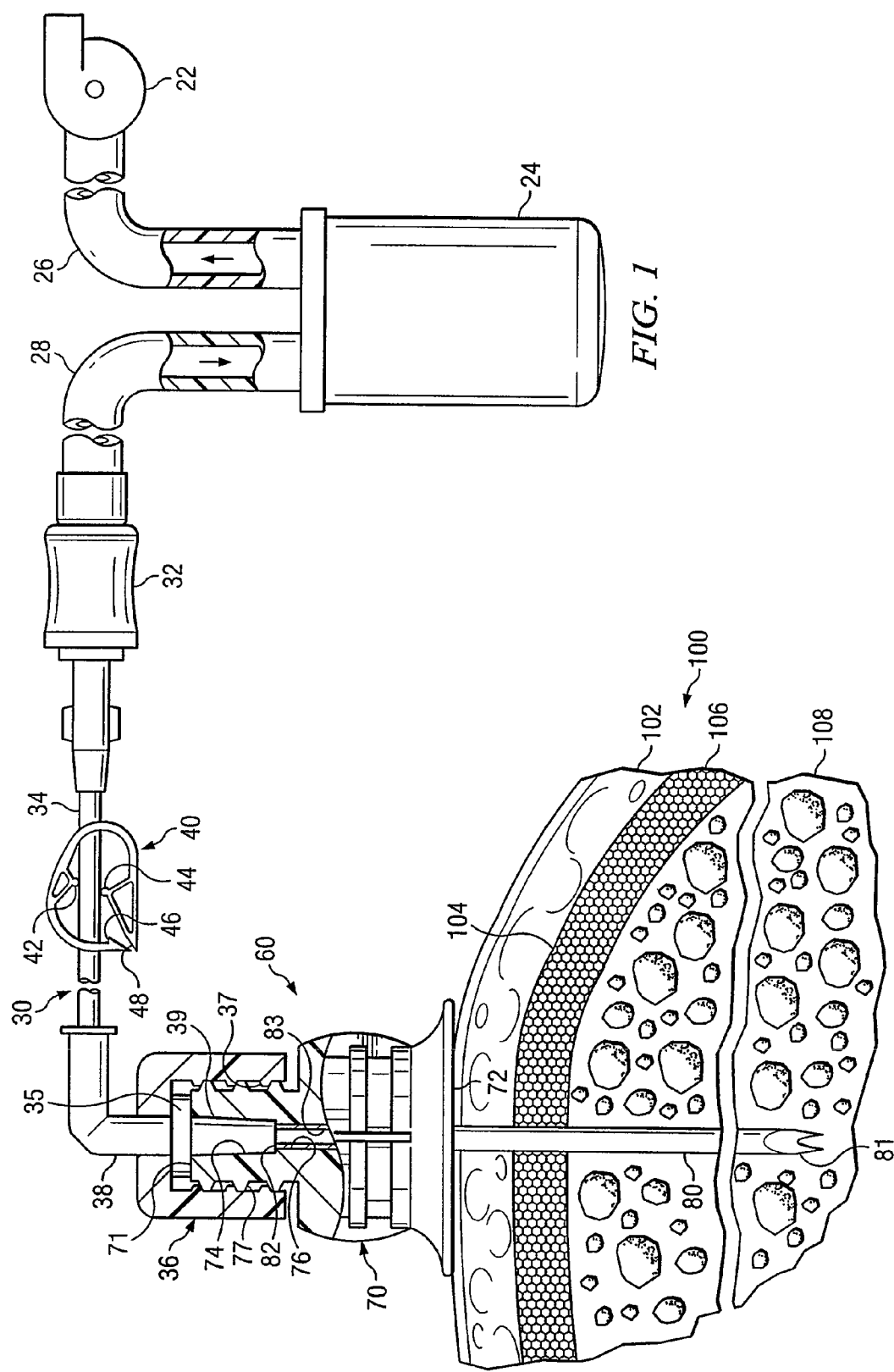
FIG. 1 is a schematic drawing in section and in elevation with portions broken away showing one example of an intraosseous device and associated equipment which may be used to aspirate bone marrow from one or more target areas in accordance with teachings of the present disclosure.
Figure 4:
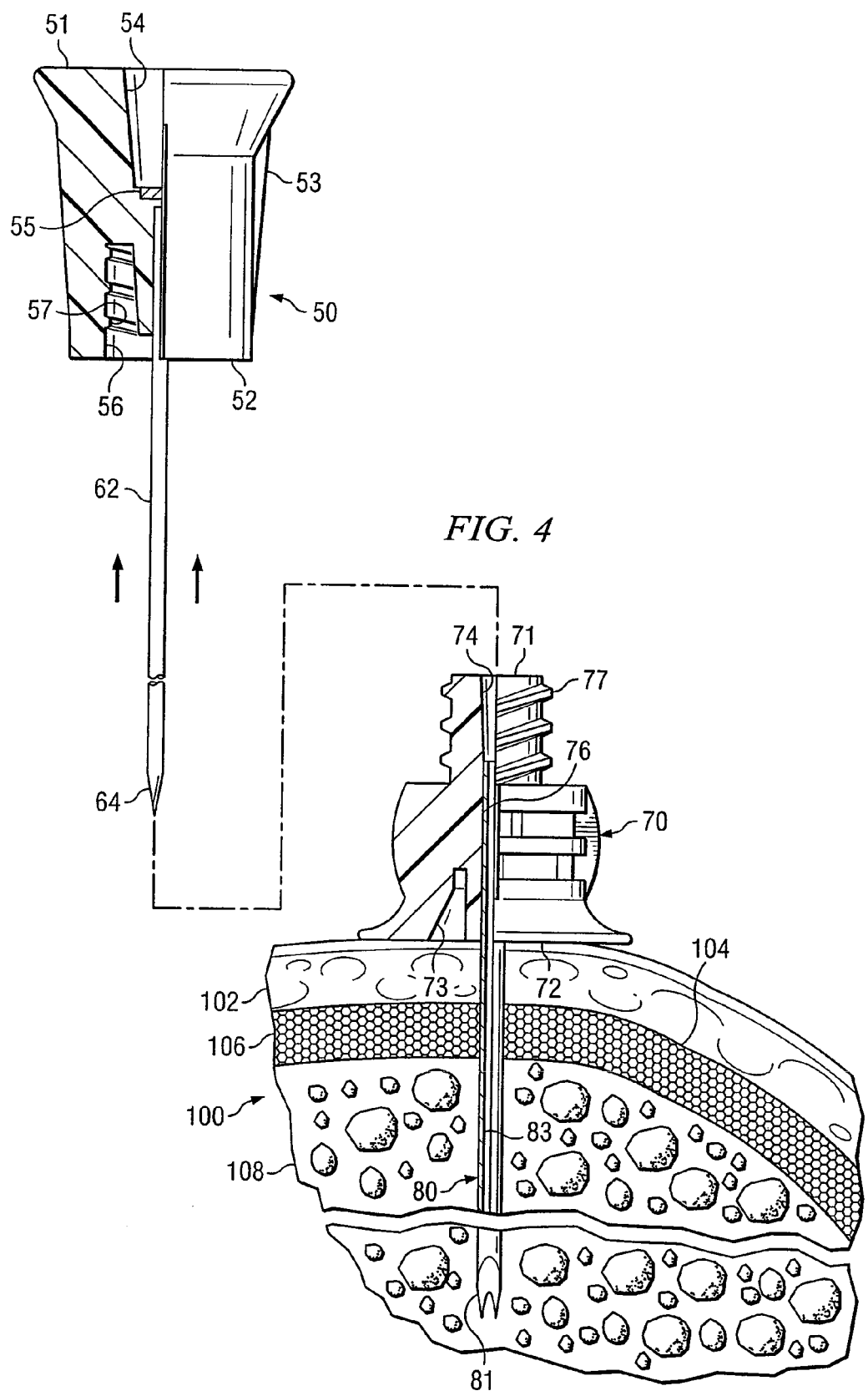
FIG. 4 is an exploded, schematic drawing in section and in elevation with portions broken away showing one example of an intraosseous device installed at a selected insertion site in accordance with teachings of the present disclosure.

The term "intraosseous (IO) device" may be used in this application to include any hollow needle, hollow drill bit, penetrator assembly, bone penetrator, cannula, trocar, inner penetrator, outer penetrator, penetrator net, IO needle or IO needle set operable to provide access to an intraosseous space or bone cavity containing bone marrow. One example of an intraosseous device inserted into bone and associated bone marrow in accordance with teachings of the present disclosure is shown in FIGS. 1 and 4.

A wide variety of trocars, spindles and/or shafts may be disposed within an outer penetrator or cannula. Such trocars, spindles and shafts may sometimes be characterized as inner penetrators. An IO device incorporating teachings of the present disclosure will generally include an outer penetrator.

An IO device incorporating teachings of the present disclosure may or may not include an inner penetrator.

The terms "insertion site," "penetration site," and "installation site" may be used in this application to describe a location on a bone at which an intraosseous device may be inserted or drilled into the bone and associated bone marrow. Insertion sites, penetration sites and installation sites are generally covered by skin and soft tissue.

The term "target area" may be used in this application to describe selected portions of a bone cavity or locations in a bone cavity from which associated bone marrow may be harvested in accordance with teachings of the present disclosure.

The terms "harvest" and "harvesting" may be used in this application to include both bone marrow biopsy and bone marrow aspiration. Bone and/or marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation and/or research purposes. For example some stem cell research techniques may require relatively large quantities of bone marrow.

Many current available techniques used to harvest bone and/or bone marrow may require more than one penetration into a bone and associated bone marrow to retrieve an adequate sample of bone and/or bone marrow. Multiple penetration sites may be required in the same bone if a biopsy sample is not satisfactorily retrieved at the first penetration site. Medical personnel may need to insert an IO needle into several different penetration sites on the same bone to obtain adequate quantities of bone marrow for transplant or stem cell research. For example obtaining sufficient quantities of bone marrow from a patient's pelvis may require six or more insertion sites. Multiple insertions may be extremely painful for a patient and may deter some people from donating bone marrow. Multiple insertions may also cause fatigue in medical personnel performing such procedures with manual IO devices.

Bone marrow transplant procedures and various research procedures such as stem cell research often require relatively large quantities of bone and/or bone marrow. Hip bones generally have a large bone cavity and are therefore frequently used as a target area for harvesting bone marrow for transplant procedures, stem cell research procedures or any other procedure requiring relatively large quantities of bone marrow.

In FIGS. 1 and 4 intraosseous device 60 is shown installed in a portion of hip bone 100 referred to as the ilium. One of the penetration sites or insertion sites frequently used for obtaining bone marrow from a hip bone may be the posterior iliac crest. See FIGS. 1 and 4. Another insertion site may be the anterior iliac crest.

Hip bone 100 may include three segments—the ilium, the ischium and the pubis. These segments are generally distinct from each other in young patients but are generally fused together in adults. Skin and soft tissue 102 generally cover insertion sites in crest 104 of the ilium. See FIGS. 1 and 4. All bones generally include a tough, hard to penetrate layer of cortex. Crest 104 typically includes cortex layer 106.

FIGS. 1 and 4 show an enlarged cortex layer for illustration purposes only. A typical thickness for skin and soft tissue layer 102 may be seven to eight millimeters (7 mm to 8 mm). A typical thickness for cortex layer 106 may be approximately two millimeters (2 mm).

As discussed later in more detail, penetrator assembly or intraosseous (IO) device 60 may be inserted in the crest of the ilium or any other insertion site with minimum trauma to obtain bone and/or bone marrow samples in accordance with teachings of the present disclosure.

Oncologists and other health care provides may be unable to successfully obtain a suitable specimen of bone and/or bone marrow because currently available biopsy needles sometimes fail to capture a specimen of bone and/or bone marrow. When a specimen is obtained, the specimen may be damaged or contaminated. An intraosseous device incorporating teachings of the present invention may substantially reduce or eliminate problems associated with obtaining a suitable specimen of bone and/or bone marrow. See for example IO devices 80*a* (FIG. 8A), 80*b* (FIG. 8B) and IO device 160 (FIGS. 9A-9D).

FIG. 1 shows one example of a system for removing bone marrow from a bone using apparatus and methods incorporating teachings of the present disclosure. Samples of bone and/or bone marrow may be obtained from any suitable bone including, but not limited to, tibia (leg bone), ilium (pelvis) or sternum (chest) using apparatus and methods incorporating teachings of the present disclosure. FIGS. 1 and 4 show intraosseous device 60 inserted into a target area in a patient's ilium.

Various features of the present disclosure may be described with respect to powered driver 200. See FIG. 2. Various features of the present disclosure may also be described with respect to intraosseous devices 60. However, teachings of the present disclosure may be satisfactorily used with a wide variety of drivers and intraosseous devices. The present disclosure is not limited to intraosseous device 60 or driver 200.

For one embodiment, system 20 may include a source of vacuum or low pressure 22, collection container 24, vacuum tubing 26 and collection tubing 28. Source of vacuum 22 may be a pump such as shown in FIG. 1 or may be a portion of a hospital or operating suite low pressure vacuum system (not expressly shown). Vacuum tubing 26 may extend between vacuum source 22 and collection container 24. Various types of tubing may be satisfactorily used to form vacuum tubing 26 and/or collection tubing 28. The length of vacuum tubing 26 and/or collection tubing 28 may be varied depending upon each facility in which system 20 is used.

Collection tubing 28 may extend between collection container 24 and intraosseous (IO) connector assembly 30. Various types of connections and connector assemblies including, but not limited to, IO connector assembly 30 may be used to communicate fluids between IO device 60 and suction tubing 28.

IO connector assembly 30 may include coupling or tubing connector 32 operable to be releasably engaged with one end of collection tubing 28 opposite from container 24. Various types of couplings associated with IV tubing may be satisfactorily used. Relatively short, flexible tubing 34 may extend between coupling 32 and right angle connector 38. For some applications, flow control stop or device 40 may be attached to flexible tubing 34 between coupling 32 and right angle connector 38.

Flow control device 40 may have a first, open position as shown in FIG. 1 and a second, closed position (not expressly shown). Flow control device 40 may be used to prevent fluid flow from IO device 60 during engagement and disengagement with collection tubing 28 or any other apparatus such as IV tubing (not expressly shown) which may be attached to IO connector assembly 30.

Flow control device 40 may be formed from relatively flexible material which allows compressing or squeezing flow control device 40 to engage notch or hook 46 with end 48. Compression of flow control device 40 will preferably result in clamps 42 and 44 compressing or closing off fluid flow through the lumen of flexible tubing 34. Engagement of notch 46 with end 48 will hold flow control stop 40 in its second, closed position.

Right angle connector 38 may be engaged with one end of flexible tubing 34 opposite from coupling 32. Right angle connector 38 allows flexible tubing 34 to be connected to IO device 60 at an angle that will generally not kink or pinch off the lumen of tubing 34. Right angle connector 38 may also include Luer fitting 39 sized to be inserted into tapered opening 74 formed in first end 71 of hub 70. See FIGS. 1 and 4.

Lock nut 36 may be disposed on the exterior of right angle connector 38 adjacent to Luer fitting 39. Flange 35 may also be formed on the exterior of right angle connector 38 adjacent Luer fitting 39. Lock nut 36 may be both rotatably and slidably disposed on the exterior of right angle connector 38 adjacent to Luer fitting 39 with flange 35 disposed between lock nut 36 and Luer fitting 39. Threads 37 formed on interior portions of lock nut 36 may be used to releasably engage right angle connector 38 with threads 77 formed adjacent to first end 71 of hub 70.

Penetrator assembly or IO device 60 as shown in FIGS. 1, 3, 4 and 6 may include connector 50 and hub 70. Connector 50 may be described as having a generally cylindrical configuration defined in part by first end 51 and second end 52. First end 51 may include opening or connector receptacle 54 disposed therein and sized to receive connector 216 of powered driver 200. See FIGS. 2 and 4.

Connector receptacle or opening 54 may be formed with various configurations and/or dimensions. One or more webs (not expressly shown) may be formed in end 51 extending from opening 54. Open segments or void spaces (not expressly shown) may be formed between such webs. Opening 54 and associated webs may be used to releasably engage connector 50 with any driver satisfactory for installing an IO device at a selected insertion site. For some applications metallic disk 55 may be disposed within opening 54 for use in releasably engaging penetrator assembly 60 with a magnet (not expressly shown) disposed on the end of connector 216.

For some applications exterior portion of connector 50 may include an enlarged tapered portion adjacent to first end 51. A plurality of longitudinal ridges 53 may also be formed on the exterior of connector 50 proximate first end 51. The enlarged tapered portion and/or longitudinal ridges 53 may allow an operator to grasp associated penetrator assembly 60 during attachment with a driver and may facilitate disengagement of connector 50 from hub 70 after outer penetrator or cannula 80 has been inserted into a bone and associated bone marrow. Connector 50 may also be used to manipulate an attached trocar or inner penetrator during harvesting of bone and/or bone marrow in accordance with teachings of the present disclosure.

Second opening 56 may be formed in second end 52 of connector 50. See FIG. 4. For some applications threads 57 may be formed on interior portions of second opening 56 extending from second end 52. Threads 57 may be sized to engage threads 77 formed on exterior portions of hub 70. Threads 57 and 77 may be characterized as forming portions of a Luer lock connection. However, the present disclosure is not limited use with threads 57 and 77. Threads 37 of lock nut 36 and threads 57 of connector 50 may have similar configurations and dimensions. Various types of releasable connections including, but not limited to, other types of Luer lock connections may be formed on adjacent portions of connector 50 and hub 70.

Trocar or inner penetrator 62 may be securely engaged with connector 50 extending from second end 52. See FIG. 4. The dimensions and configuration of inner penetrator 62 may be selected to allow inner penetrator 62 to be slidably inserted into longitudinal bore 83 of outer penetrator or cannula 80. Trocar 62 may include first end or tip 64. The dimensions and configuration of tip 64 may be selected to accommodate inserting penetrator assembly 60 into bone and associated bone marrow at a selected penetration site.

Inner penetrator or trocar 62 and outer penetrator or cannula 80 may have sufficient length to allow harvesting bone marrow at target areas in a hip bone located four or five inches from an associated penetration site. Inner penetrator 62 and/or outer penetrator 80 may have a length of six (6) inches or more. For some applications outer penetrator 80 may be generally described as a hollow IO needle.

Hub 70 may include first end 71 and second end 72. See FIGS. 1 and 4. First end 71 of hub 70 may have a generally cylindrical pin-type configuration compatible with releasably engaging hub 70 with second end or box end 52 of connector 50 and lock nut 36. As previously noted, threads 77 formed adjacent to end 71 of hub 70 may be releasably engaged with threads 57 formed on interior portions of opening 56 of connector 50 and threads 37 formed on interior portions of lock nut 36.

For some applications second end 72 of hub 70 may have the general configuration of a flange. The dimensions and configuration of second end 72 of hub 70 may be varied to accommodate associated insertion sites. Hub 70 may be formed with a wide variety of flanges or other configurations compatible with contacting a patient's skin adjacent a respective insertion site.

Passageway 76 may extend from first end 71 through hub 70 to second end 72. Portions of passageway 76 spaced from second end 72 may have dimensions selected to be compatible with securely engaging exterior portions of outer penetrator or cannula 80 with hub 70. Second end 82 of cannula 80 may be disposed within passageway 76 between first end 71 and second end 72.

First end 81 of cannula 80 may extend from second end 72 of hub 70. Portions of passageway 76 extending from first end 71 of hub 70 may have an enlarged inside diameter to accommodate attachment with various types of fluid connectors. For example, see Luer fitting 39 formed on one end of right angle connector 38 in FIG. 1.

Cannula or outer penetrator 80 may have longitudinal bore 83 extending from first end or tip 81 to second end 82. First end 81 may have an opening to allow fluid communication therethrough. End 64 of inner penetrator 62 may also extend through the opening in end 81 of outer penetrator 80. See FIGS. 3 and 5A. Exterior dimensions of trocar or inner penetrator 62 are preferably selected to allow inner penetrator 62 to be inserted through outer penetrator 80 with first end 64 of inner penetrator 62 generally aligned with first end 81 of outer penetrator 80 after threads 77 have been engaged with threads 57. See FIGS. 3 and 5A.

Tip 81 of outer penetrator 80 and/or tip 64 of inner penetrator 62 may be operable to penetrate bone and associated bone marrow. The configuration and dimensions of tip 81 may be selected to allow inserting outer penetrator 80 into a bone and associated bone marrow without the use of inner penetrator 62. However, placing tip 64 within tip 81 may substantially increase stability and minimize any tendency of outer penetrator 80 to wobble during insertion of IO device 60 into a bone and associated bone marrow. The use of inner penetrator 62 with tip 64 may be particularly beneficial during penetration of a cortex layer covering a bone.

The configuration of tips 81 and 64 may be selected to penetrate a bone, bone marrow and other portions of a patient's body with minimum trauma. Tip 64 of inner penetrator 62 may have various shapes such as a generally trapezoid shape with one or more cutting surfaces. For some applications tips 81 and 64 may be ground together as a single unit during an associated manufacturing process. See FIG. 5A.

Outer penetrator 80 and/or inner penetrator 62 may be formed from various materials including, but not limited to, stainless steel, titanium or any other material having suitable strength and durability to penetrate bone and associated bone marrow. The combination of hub 70 with cannula 80 may sometimes be referred to as an "intraosseous needle." The combination of trocar 62 with cannula 80 may sometimes be referred to as a "penetrator set" or an "IO needle set."

Hub 70 and particularly second end or flange 72 may be used to stabilize intraosseous device 60 after insertion into a bone and associated bone marrow. Second end 52 of connector 50 may be releasably engaged from first end 71 of hub 70 after insertion of outer penetrator 80 into associated bone marrow. See FIG. 4. The depth of such insertion will be dependent upon the distance between tip 81 of cannula 80 and flange 72 of hub 70. Annular slot or groove 73 may be formed within second end 72 and sized to receive one end of a protective cover or needle cap (not expressly shown). Slot or groove 73 may be used to releasably engage a protective cover with penetrator assembly 60.

Powered driver 200, as shown in FIG. 2, may include housing 202 with various types of motors and/or gear assemblies disposed therein (not expressly shown). A rotatable shaft (not expressly shown) may be disposed within housing 202 and connected with a gear assembly (not expressly shown). Various types of fittings, connections, connectors and/or connector receptacles may be provided at one end of the rotatable shaft extending from end 204 of housing 202.

For some applications pin type fitting or connector 216 may be formed on the one end of the rotatable shaft. A matching box type fitting or connector receptacle may be provided on an intraosseous device so that connector 216 of powered driver 200 may be releasably engaged with the intraosseous device. For some applications, connector 216 may have a pentagonal shaped cross section with tapered surfaces formed on the exterior thereof.

Handle 206 may include a battery (not expressly shown) or other power source. Handle 206 may also include trigger assembly 208 for use in activating powered driver 200. Examples of powered drivers are shown in pending patent application Ser. No. 10/449,503 filed May 30, 2003 entitled "Apparatus and Method to Provide Emergency Access To Bone Marrow," now U.S. Pat. No. 7,670,328; Ser. No. 10/449,476 filed May 30, 2003 entitled "Apparatus and Method to Access Bone Marrow," now U.S. Pat. No. 7,699,850; and Ser. No. 11/042,912 filed Jan. 25, 2005 entitled "Manual Intraosseous Device," now published as Pub. No. US 2005/0165404.

FIG. 4 shows inner penetrator 62 removed from outer penetrator 80. A cap (not expressly shown) will generally be placed over end 71 of hub 70 unless IO connector assembly 30 will be promptly engaged with end 71 of hub 70 or another penetrator or trocar will be promptly inserted into outer penetrator 80. Such caps are frequently used with biopsy needles and other types of intraosseous devices to prevent undesired fluid communication therethrough.

After inner penetrator 62 has been removed from outer penetrator 60, lock nut 36 may be used to releasably engage IO connector assembly 30 with end 71 of hub 70. See FIG. 1.

Figure 8A:
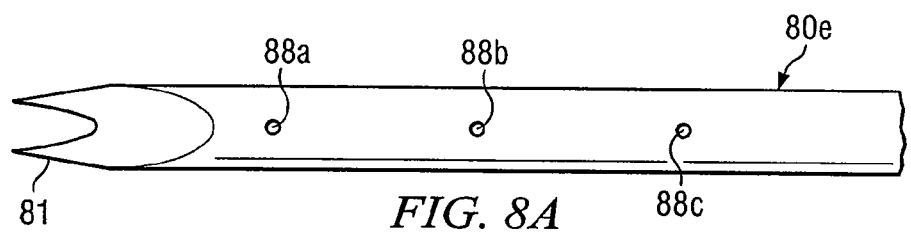
FIG. 8A is a schematic drawing showing an isometric view with portions broken away of an outer penetrator or cannula operable to harvest bone marrow at selected target areas in accordance with teachings of the present disclosure.
Figure 8B:
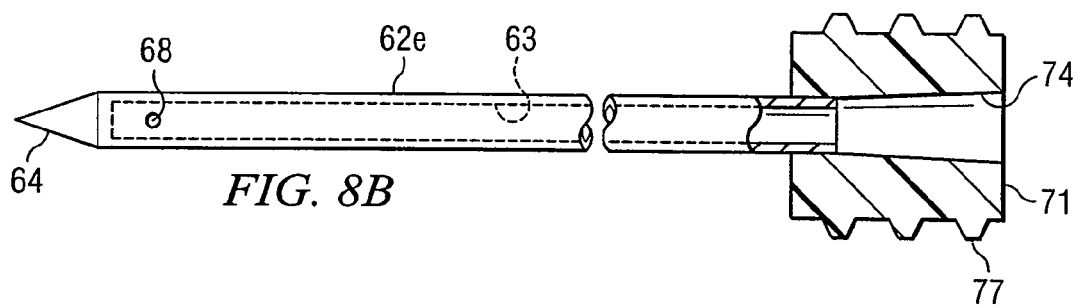
FIG. 8B is a schematic drawing showing an isometric view with portions broken away of an inner penetrator or trocar operable to harvest bone marrow in accordance with teachings of the present disclosure.

Other types of penetrators and trocars may also be inserted through opening 74 of hub 70 and longitudinal bore 83 of outer penetrator 80. Inner penetrator 62*e* as shown in FIG. 8B and trocar 162 as shown in FIGS. 9A-9D are examples of two such devices which may be inserted through opening 74 in hub 70 and longitudinal bore 83 of outer penetrator 80.

Figure 5A:
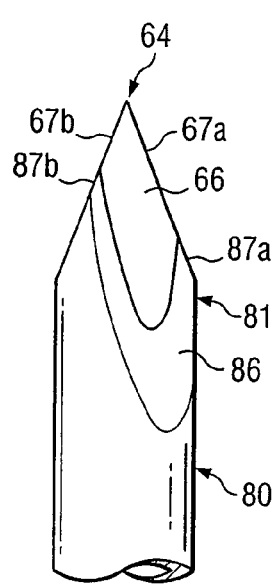
FIG. 5A is an enlarged schematic drawing with portions broken away showing an isometric view of one example of a bone cutting tip formed on an intraosseous device.

FIG. 5A shows tip 64 of inner penetrator 62 and tip 81 of outer penetrator 80 disposed immediately adjacent to each other after having been ground to form machined cutting surfaces 66 and 86. Grinding tips 64 and 81 as a single unit may also result in forming associated cutting edges 67*a* and 87*a* and associated cutting edges 67*b* and 87*b*. Providing a matching fit allows respective tips 81 and 64 to act as a single drilling unit to minimize trauma at an insertion site as portions of penetrator assembly 60 are inserted into a bone and associated bone marrow. Cutting surfaces 66 and 86, associated cutting edges 67*a* and 87*a* and associated cutting edges 67*b* and 87*b* may be particularly beneficial for use in cutting the cortex layer covering a bone. For some applications installing inner penetrator 62 with tip 64 within outer penetrator 80 and tip 81 may substantially reduce and/or eliminate any tendency of IO device 60 to wobble while being inserted or drilled through a cortex layer.

Figure 5B:
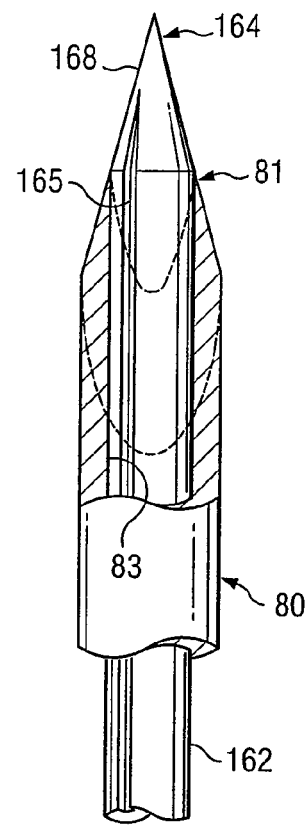
FIG. 5B is a schematic drawing with portions broken away showing an isometric view of another example of a bone cutting tip formed on an intraosseous device.
Figure 6:
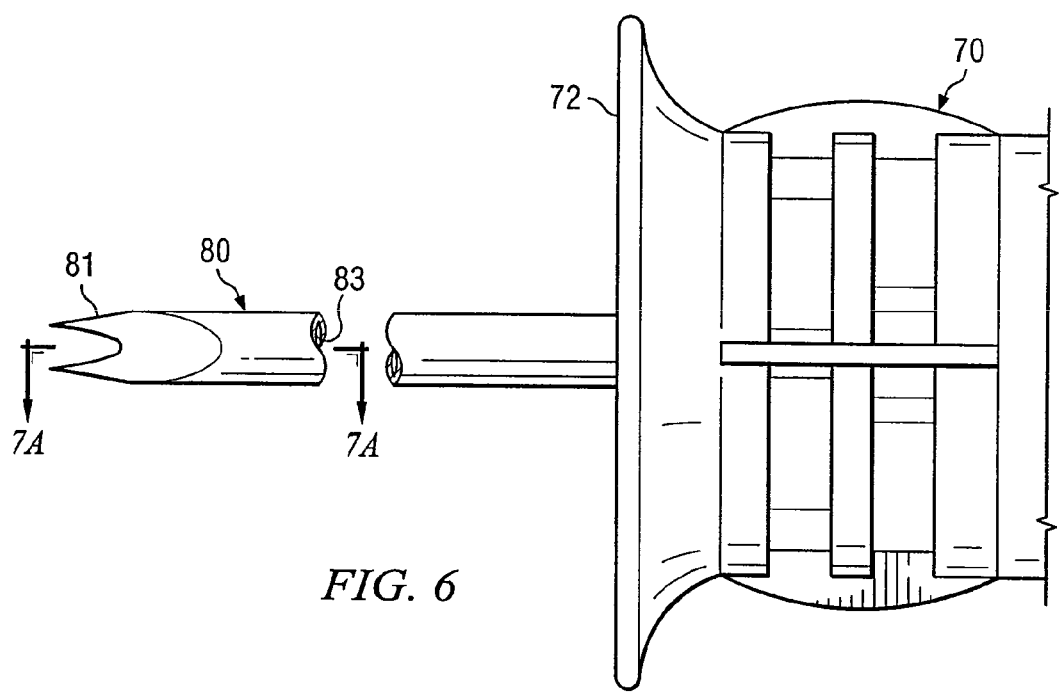
FIG. 6 is an enlarged schematic drawing showing an isometric view with portions broken away of an intraosseous device incorporating teachings of the present disclosure.

Sometimes a longitudinal groove may run along one side of an inner penetrator to allow bone chips and/or tissue to exit an insertion site as a penetrator assembly is drilled deeper into bone and associated bone marrow. FIG. 5B shows inner penetrator 162 slidably disposed within outer penetrator 80. First end or tip 164 of inner penetrator 162 may be disposed adjacent to first end or tip 81 of outer penetrator 80. Tips 164 and 81 may have matching machined surfaces and cutting edges as previously described with respect to tip 64 and 81. Longitudinal groove 165 formed in inner penetrator 162 may extend from tip 164. Longitudinal groove or slot 165 may run along the side of trocar 162 to allow bone marrow and/or tissue to exit an insertion site as an associated intraosseous device is installed at an insertion site.

For some applications an outer penetrator or cannula incorporating teachings of the present disclosure may include an interior threaded portion to grab or "purchase" a bone specimen as an IO device is inserted into a bone. The use of a powered driver may increase effectiveness of an IO device having such interior threads to reliably collect a bone specimen on the first insertion into a bone.

Bone cells function as progenitor cells to produce or manufacture red and white cells for associated bone marrow. As a result, clinicians and medical technologists often use small pieces of bone (spicules) to determine if normal, disease free bone anatomy and architecture are present at an insertion site. A sample of only bone marrow does not satisfactorily indicate the condition of the bone which produced the bone marrow. A bone marrow sample may not indicate the presence of cancer or other diseases (particularly at an early stage) in an associated bone.

Various features of outer penetrators 80*a* and 80*b* may be described with respect to penetrating cortex layer 106 and adjacent portions of bone 100 and bone marrow 108 as shown in FIGS. 1 and 4. However, intraosseous devices incorporating teachings of the present disclosure as shown in FIGS. 7A-7D may be used to obtain bone and/or bone samples from a wide variety of insertion sites and target areas. Teachings of the present disclosure are not limited to the iliac crest or hip bones.

Figure 7A:
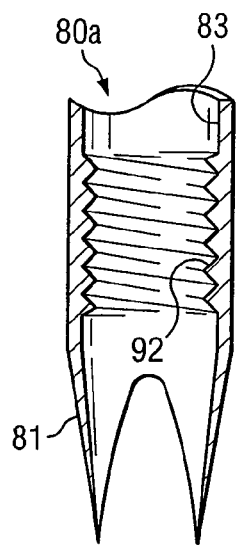
FIG. 7A is a schematic drawing in section with portions broken away taken along line 7A-7A of FIG. 6 showing one example of an intraosseous device operable to obtain a bone sample in accordance with teachings of the present disclosure.

FIG. 7A shows outer penetrator 80*a* having internal threads 92 disposed adjacent to first end or tip 81. Threads 92 may be sized to be releasably engaged with a sample of bone and/or bone marrow during rotation of outer penetrator 80*a* by a powered driver. After outer penetrator 80a and previously described inner penetrator 62 or any other suitable penetrator have been inserted through cortex layer 106 inner penetrator 62 may be withdrawn. A suitable connector such as a second connector 50 without inner penetrator 62 attached thereto (not expressly shown) may be used to re-engage powered driver 200 with hub 70. Powered driver 200 may then be used to continue inserting outer penetrator 80a into the desired insertion site which will result in first end or tip 81 coring portions of bone and/or bone marrow adjacent to cortex layer 106.

Continued rotation of outer penetrator 80a will result in threads 92 securely engaging the bone specimen within longitudinal bore 83 of outer penetrator 80a. Outer penetrator 80a may then be disconnected from powered driver 200. Hub 70 may be used to disengage or withdraw outer penetrator 80a from the insertion site. The bone and/or bone marrow sample may be removed from longitudinal bore 83 by inserting an appropriately sized rod (not expressly shown) through first end 81 of outer penetrator 80a. The rod may be used to push the bone and/or bone marrow sample through longitudinal bore 83 and out of second end 82.

Figure 7B:
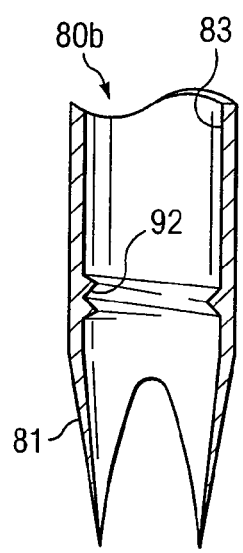
FIG. 7B is a schematic drawing in section with portions broken away showing another example of an intraosseous device operable to obtain a bone sample in accordance with teachings of the present disclosure.

One of the benefits of the present disclosure includes the ability to modify internal thread designs and/or limit the number of threads to optimize retention of a bone or bone marrow sample and at the same time minimize damage which may occur to a bone and/or bone marrow sample during removal from an associated outer penetrator or cannula. For example outer penetrator 80b as shown in FIG. 7B may include only one or two threads 92 formed within longitudinal bore 83 adjacent to first end 81 as compared with multiple threads 92 disposed within outer penetrator 80a as shown in FIG. 7A. A bone and/or bone marrow sample may often be more easily disengaged from one or two threads 92 as compared to the larger number of threads 92 shown in outer penetrator 80a. Respective threads 92 contained in outer penetrators 80a and 80b may substantially reduce or eliminate failed attempts to remove a bone sample and/or bone marrow from a target area.

One of the features of the present disclosure may include sampling multiple target areas while at the same time installing or inserting an intraosseous device into only a single penetration site. For example outer penetrator or cannula 80e as shown in FIG. 8A may include multiple sampling ports or side ports formed in the exterior thereof. For embodiments such as shown in FIG. 8A outer penetrator or cannula 80e may include sampling ports or side ports 88a, 88b and 88c which extend laterally from longitudinal bore 83 to the exterior of outer penetrator 80e.

Sampling ports 88a, 88b and 88c may each be operable to provide access to three separate target areas for aspiration of bone marrow. Conventional biopsy needles would generally require using three separate insertion sites in a bone to provide access to three separate target areas in the bone marrow of a hip bone or other bones.

Inner penetrator or trocar 62e as shown in FIG. 8B may include longitudinal bore 63 extending from first end 64 to second end 69 of inner penetrator 62e. Sampling port or side port 68 may be formed in inner penetrator 62e proximate first end 64. Sampling port 68 may be used to communicate fluids and/or bone marrow samples between the exterior of inner penetrator 62a and longitudinal bore 63.

Various types of connections may be provided on second end 69 of inner penetrator 62e. For embodiments such as shown in FIG. 8B a Luer type connection represented by threads 77 and opening 74 may be disposed proximate end 71. A wide variety of tubing connectors and various types of bone marrow aspiration equipment may be releasably engaged with end 71 of inner penetrator 62e. Various techniques and procedures may be satisfactorily used to selectively align sampling port 68 with respective sampling ports 88a, 88b and 88c. When sampling port 68 of inner penetrator 62a is respectively aligned with sampling port 88a, 88b or 88c of outer penetrator 80e, respective portions of bone marrow may be suctioned from adjacent target areas.

Generally only a limited volume (a few cubic centimeters) of bone marrow may be retrieved from any one target area before systemic blood begins to enter the target area and will often be retrieved with the bone marrow sample. Therefore, aspiration of bone marrow from multiple target areas is generally required to obtain larger volumes of bone marrow. Forming multiple sampling ports or side ports in an intraosseous device in accordance with teachings of the present disclosure may allow retrieving multiple bone marrow samples from a single insertion site. For example, three sample ports or three side ports may allow retrieving three times the volume of bone marrow samples as compared with using a conventional biopsy needle at the same insertion site. The total number of insertions of an intraosseous device incorporating teachings of the present disclosure may be substantially reduced while still allowing accumulation of relatively large samples of bone marrow for transplantation, diagnostic and/or research procedures.

Figure 8C:
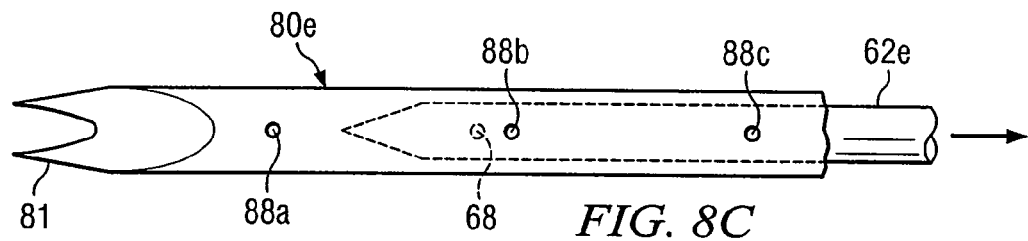
FIG. 8C is a schematic drawing with portions broken away showing an isometric view of an intraosseous device having an outer penetrator and an inner penetrator operable to harvest bone marrow at selected target areas in accordance with teachings of the present disclosure.

For embodiments such as shown in FIGS. 8A, 8B and 8C removable trocar 62e may be inserted into longitudinal bore 83 of outer penetrator 80e. Sampling port 68 may be aligned with sampling port 88a of outer penetrator 80e. Suction or low pressure vacuum may then be applied to end 71 of the Luer type connection attached to removable trocar 62e. Bone marrow samples may be removed from a target area adjacent to side port 88a until undesired quantities of systemic blood appear in the bone marrow sample. After removing an appropriate amount of bone marrow from side port 88a, removable trocar 62e may be moved to a position adjacent to sampling port 88b. The same procedure may be repeated to remove an appropriate amount of bone marrow from a target area adjacent to sampling port 88b. The same sampling procedure may be repeated at sampling port 88c and any other sampling port or ports formed in exterior portions of outer penetrator 80e.

Currently available instruments used to obtain samples of bone and/or bone marrow frequently have less than desired ability and reliability to engage and satisfactorily withdraw a sample of bone and/or associated bone marrow. Currently available instruments satisfactory for grasping a bone specimen may not be satisfactory for grasping a more fluid sample of bone marrow. One aspect of the present disclosure includes providing a trocar having one end which may be opened and closed to securely grasp a sample of bone and/or bone marrow.

FIG. 9A-9D show one example of an IO device having a sample chamber or specimen cavity defined in part by a trocar having one end incorporating teachings of the present disclosure. IO device 160 as shown in FIGS. 9A-9D may include outer penetrator or cannula 180 and trocar 162. Outer penetrator or cannula 180 may include longitudinal bore 183 extending from first end 181 to a second end (not expressly shown). Longitudinal bore 183 may include enlarged inside diameter portion 183a disposed adjacent to and extending from first end 181. Longitudinal bore 183 may also include reduced inside diameter portion 183b extending from the second end of outer penetrator 180 towards first end 181. Longitudinal bore 183 may also include transition portion or tapered inside diameter portion 183c extending between enlarged inside diameter portion 183a and reduced inside diameter portion 183b. See FIGS. 9A and 9B.

An inner penetrator such as previously described inner penetrator 62 may be disposed within longitudinal bore 183 during installation of intraosseous device 160 at a penetration site. The inner penetrator may be removed from outer penetrator 180 when first end 181 is located at a desired target area for obtaining a bone marrow specimen. Trocar 162 may next be slidably disposed in longitudinal bore 183. See FIGS. 9A and 9B.

Trocar 162 will generally have a length greater than the length of outer penetrator 180. As a result, first end 161 of trocar 162 may extend from first end 181 of outer penetrator 180. Trocar 162 may also include a second end (not expressly shown) which extends from the second end of outer penetrator 180. Connector 50 or any other suitable handle (not expressly shown) may be attached to the second end of trocar 162 for use in manipulating trocar 162.

For some applications inner trocar 162 may be described as having a "split end" configuration or a "split needle" configuration. See FIGS. 9A and 9D. For some applications trocar 162 may be a generally hollow tube extending from first end 161 to the second end. For other applications portions of trocar 162 adjacent to the second end may be a generally solid rod or shaft (not expressly shown).

As shown in FIGS. 9A-9D trocar 162 may include split ends 164a and 164b defined in part by first segment 165a and second segment 165b extending from first end or tip 164. First segment 165a and second segment 165b may sometimes be described as "jaws". Respective cavities 163a and 163b defined in part by interior portions of first segment 165a and second segment 165b may be formed adjacent to split ends 164a and 164b. Segments 165a and 165b may be relatively thin which allow segments 165a and 165b to flex relative to each other and to flex relative to adjacent portions of outer penetrator 180.

Respective bump or enlargement 166a may be formed on exterior portions of first segment 165a spaced from first end or tip 164a. A similar bump or enlargement 166b may be formed on exterior portions of second segment 165b spaced from tip 164b. Enlargements 166a and 166b may sometimes be referred to as "knobs". The dimensions and configuration of enlargements 166a and 166b may be selected to be compatible with longitudinal movement of trocar 162 within reduced inside diameter portion 183b of cannula 180. See FIG. 9B.

When the first end 164 of trocar 162 extends from first end 181 of cannula 180, enlargements 166a and 166b may expand radially outward into enlarged inside diameter portion 183a. Tips 164a and 164b may then be inserted into bone marrow at a target area adjacent to end 181. As trocar 162 is withdrawn from an extended, open position (see FIG. 9A) to a retracted, closed position (see FIG. 9B), tips 164a, 164b and associated jaws 165a and 165b may cooperate with each other to break loose bone marrow specimen 108a and capture bone marrow specimen 108a within the sample cavity or sample chamber formed by jaws 165a and 165b. As trocar 162 is further withdrawn from longitudinal bore 183, enlargements 166a and 166b will contact reduced inside diameter 183b to maintain bone marrow specimen 108a securely captured within trocar 162.

Figure 9A:
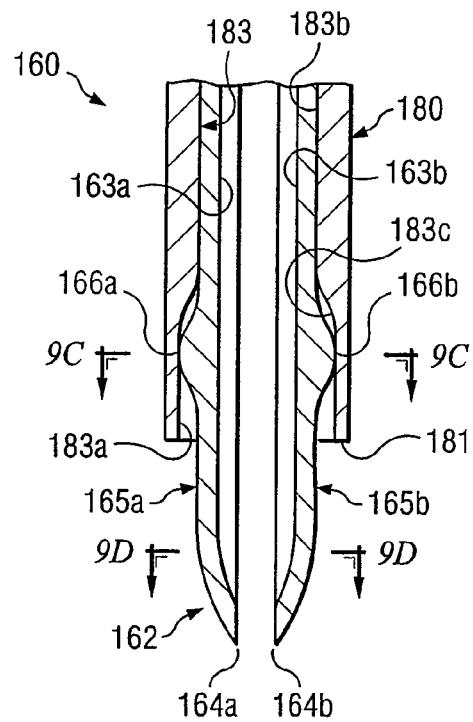
FIG. 9A is a schematic drawing in section with portions broken away showing one example of an intraosseous device in an open position prior to obtaining a biopsy sample in accordance with teachings of the present disclosure.
Figure 9B:
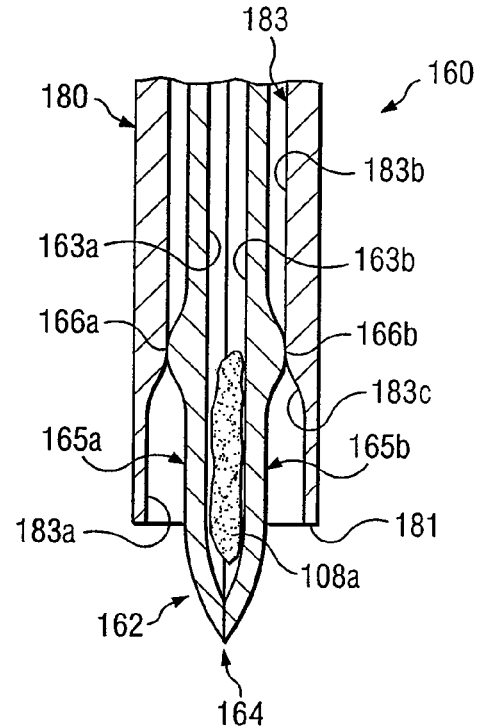
FIG. 9B is a schematic drawing in section with portions broken away showing the intraosseous device of FIG. 9A in a closed position after obtaining a biopsy sample in accordance with teachings of the present disclosure.
Figure 9C:
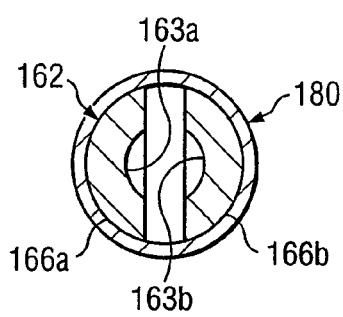
FIG. 9C is a schematic drawing in section taken along lines 9C-9C of FIG. 9A.
Figure 9D:
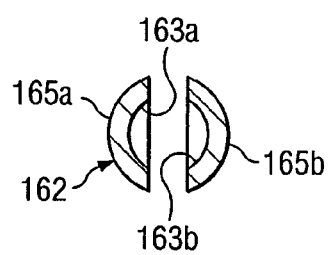
FIG. 9D is a schematic drawing in section taken along lines 9D-9D of FIG. 9A.

FIGS. 9A, 9C and 9D show various portions of outer penetrator 180 and trocar 162 with first end or tip 164 of trocar 162 in an open position operable to be inserted into bone marrow at a target area adjacent to first end 181 of outer penetrator 180. FIG. 9B shows inner trocar 162 in a retracted position with bone marrow specimen 108a securely engaged within a sample cavity or sample chamber defined in part by segments or jaws 165a and 165b. FIGS. 9C and 9D show respective cross-sections of the "split needle" configuration associated with trocar 162.

Although the present disclosure and its advantages have been described in detail, it should be understood that various changes, substitutions and alternations can be made herein without departing from the spirit and scope of the disclosure as defined by the following claims.

What is claimed is:

1. A hollow drive shaft assembly operable to penetrate a bone and associated bone marrow comprising:

an outer hollow drive shaft operable to penetrate the bone and associated bone marrow;

the outer hollow drive shaft operable to be rotated by a motor;

an inner channel formed in the outer hollow drive shaft;

the inner channel of the outer hollow drive shaft operable to convey specimens of bone and associated bone marrow therethrough;

a first gear attached to the outer hollow drive shaft;

the first gear engaged with a second gear attached to the motor to rotate the outer hollow drive shaft;

an inner channel formed in the outer hollow drive shaft;

the inner channel of the outer hollow drive shaft operable to convey specimens of bone and associated bone marrow therethrough;

the outer hollow drive shaft having a first end operable to penetrate the bone and associated bone marrow;

the outer hollow drive shaft having a second end operable to retrieve specimens of bone and the associated bone marrow;

a plurality of sampling ports formed in the outer hollow drive shaft spaced from the first end, the sampling ports operable to provide access to the associated bone marrow;

a removable inner trocar disposed in the inner channel of the outer hollow drive shaft;

a sampling port formed in the removable inner trocar spaced from a first end of the inner trocar, the sampling port of the removable inner trocar operable to be aligned with respective sampling ports of the outer hollow drive shaft;

a ratcheted gear attached to the trocar; and the ratcheted gear operable to change the depth of sampling from the bone marrow.

2. A hollow drive shaft assembly operable to penetrate a bone and associated bone marrow comprising:

an outer hollow drive shaft operable to penetrate the bone and associated bone marrow;

the outer hollow drive shaft operable to be rotated by a motor;

an inner channel formed in the outer hollow drive shaft;

the inner channel of the outer hollow drive shaft operable to convey specimens of bone and associated bone marrow therethrough;

a first gear attached to the outer hollow drive shaft;

the first gear engaged with a second gear attached to the motor to rotate the outer hollow drive shaft;

an inner channel formed in the outer hollow drive shaft;

the inner channel of the outer hollow drive shaft operable to convey specimens of bone and associated bone marrow therethrough;

the outer hollow drive shaft having a first end operable to penetrate the bone and associated bone marrow;

the outer hollow drive shaft having a second end operable to retrieve specimens of bone and the associated bone marrow;

a plurality of sampling ports formed in the outer hollow drive shaft spaced from the first end, the sampling ports operable to provide access to the associated bone marrow;

a removable inner trocar disposed in the inner channel of the outer hollow drive shaft;

a sampling port formed in the removable inner trocar spaced from a first end of the inner trocar, the sampling port of the removable inner trocar operable to be aligned with respective sampling ports of the outer hollow drive shaft;

a first thrust bearing and a second thrust bearing disposed on exterior portions of the outer hollow drive shaft;

the first and second thrust bearings spaced from each other; and the first and second thrust bearings operable to absorb pressure from the outer hollow drive shaft drilling into the bone.

3. The hollow drive shaft assembly of claim 2 further comprising:

an operating mechanism operable to manipulate the removable inner trocar and change the depth of taking specimens in associated bone marrow.

4. A hollow drive shaft assembly operable to remove bone marrow from a bone for diagnostic or therapeutic purposes comprising:

an outer hollow drive shaft operable to penetrate the bone and associated bone marrow;

the outer hollow drive shaft operable to be rotated by a motor;

the outer hollow drive shaft having an inner channel operable to convey bone marrow specimens therethrough for diagnostic or therapeutic purposes;

the outer hollow drive shaft having one end operable to penetrate the bone in response to rotation of the outer hollow drive shaft;

a connector disposed on an opposite end of the outer hollow drive shaft;

the connector operable to allow the outer hollow drive shaft to be connected with a suction apparatus to assist in obtaining a bone marrow specimen;

the outer hollow drive shaft further comprises a body having at least one side port operable to obtain portions of the associated bone marrow;

a removable trocar having a tip with a cutting edge; and the removable trocar further comprises at least one side port operable to obtain specimens of the associated bone marrow.

5. The hollow drive shaft assembly of claim 4, wherein the at least one side port of the outer hollow drive shaft comprises a plurality of side ports;

wherein the at least one side port of the removable trocar may be aligned with the plurality of side ports of the outer hollow drive shaft after placement of the intraosseous device in bone to allow displacement of fluids or bone marrow samples through a longitudinal bore of the removable trocar.

6. The hollow drive shaft assembly of claim 4, wherein the plurality of side ports of the outer hollow drive shaft comprises at least three side ports.

7. The hollow drive shaft assembly of claim 4, further comprising a Luer type connection disposed proximate and end of the removable trocar.

8. The hollow drive shaft assembly of claim 4, further comprising a tubing connector releasably engaged with an end of the removable trocar.

9. The hollow drive shaft assembly of claim 4, further comprising a bone marrow aspiration device releasably engaged with an end of the removable trocar.

10. A hollow drive shaft assembly operable to remove bone marrow from a bone for transplantation purposes comprising:

an outer hollow drive shaft operable to penetrate the bone and bone associated marrow;

the outer hollow drive shaft operable to be rotated by a motor;

the outer hollow drive shaft having a respective inner channel operable to convey bone marrow specimens therethrough for transplantation purposes;

a removable trocar having a respective inner channel;

the removable trocar slidably disposed in the respective inner channel of the outer hollow drive shaft;

the removable trocar having at least one side port operable to obtain bone marrow specimens the associated bone marrow for transplantation purposes; and the outer hollow drive shaft having one end operable to penetrate the bone in response to rotation of the outer hollow drive shaft.

11. The hollow drive shaft assembly of claim 10, where the outer penetrator comprises a plurality of outer sampling ports formed in an exterior side thereof;

wherein the at least one side port of the removable trocar may be aligned with the outer sampling ports after placement of the intraosseous device in bone to allow displacement of fluids or bone marrow samples through the longitudinal bore of the removable trocar.

12. The hollow drive shaft assembly of claim 10, wherein the plurality of outer sampling ports comprises at least three outer sampling ports.

13. The hollow drive shaft assembly of claim 10, further comprising a Luer type connection disposed proximate and end of the removable trocar.

14. The hollow drive shaft assembly of claim 10, further comprising a tubing connector releasably engaged with an end of the removable trocar.

15. The hollow drive shaft assembly of claim 10, further comprising a bone marrow aspiration device releasably engaged with an end of the removable trocar.

* * * * *

UNITED STATES PATENT AND TRADEMARK OFFICE
CERTIFICATE OF CORRECTION

| | | |
|---|---|---|
| PATENT NO. | : 8,690,791 B2 | Page 1 of 1 |
| APPLICATION NO. | : 12/427310 | |
| DATED | : April 8, 2014 | |
| INVENTOR(S) | : Larry J. Miller | |

It is certified that error appears in the above-identified patent and that said Letters Patent is hereby corrected as shown below:

In the Claims

In Claim 7 on column 16, line 9, delete "and end" and insert --to an end-- therefor.

In Claim 10 on column 16, line 30, --specimens the-- should read "specimens from the".

In claim 13 on column 16, line 48, delete "and end" and insert --to an end-- therefor.

Signed and Sealed this
Twenty-second Day of July, 2014

Michelle K. Lee
*Deputy Director of the United States Patent and Trademark Office*